United States Patent
Bledsoe

(10) Patent No.: US 8,613,762 B2
(45) Date of Patent: Dec. 24, 2013

(54) COLD THERAPY APPARATUS USING HEAT EXCHANGER

(75) Inventor: Gary R. Bledsoe, Mansfield, TX (US)

(73) Assignee: Medical Technology Inc., Grand Prairie, TX (US)

( * ) Notice: Subject to any disclaimer, the term of this patent is extended or adjusted under 35 U.S.C. 154(b) by 333 days.

(21) Appl. No.: 12/973,476

(22) Filed: Dec. 20, 2010

(65) Prior Publication Data

US 2012/0158103 A1   Jun. 21, 2012

(51) Int. Cl.
  *A61F 7/00* (2006.01)
  *F28F 7/00* (2006.01)

(52) U.S. Cl.
  USPC .............................. 607/104; 607/108; 165/46

(58) Field of Classification Search
  USPC ............................................ 607/104; 165/46
  See application file for complete search history.

(56) References Cited

U.S. PATENT DOCUMENTS

| | | | |
|---|---|---|---|
| 222,690 A | 12/1879 | Goldschmidt |
| 1,896,953 A | 5/1931 | Hassell |
| 2,260,134 A | 10/1939 | Ballman |
| 2,726,658 A | 12/1955 | Chesseu |
| 3,316,732 A | 5/1967 | Burton |
| 3,587,577 A | 6/1971 | Solyanka |
| 3,625,279 A | 12/1971 | Mayo |
| 3,648,765 A | 3/1972 | Starr |
| 3,744,555 A | 7/1973 | Fletcher et al. |
| 3,811,431 A | 5/1974 | Apstein |
| 3,892,229 A | 7/1975 | Taylor et al. |
| 3,901,221 A | 8/1975 | Nicholson et al. |
| 3,918,458 A | 11/1975 | Nethery |
| 3,942,518 A | 3/1976 | Tenteris et al. |
| 3,967,627 A * | 7/1976 | Brown .......................... 607/104 |
| 3,971,398 A | 7/1976 | Taylor et al. |
| 3,993,053 A | 11/1976 | Grossan |
| 4,013,069 A | 3/1977 | Hasty |
| 4,030,488 A | 6/1977 | Hasty |
| 4,149,529 A | 4/1979 | Copeland et al. |
| 4,156,425 A | 5/1979 | Arkans |
| 4,186,732 A | 2/1980 | Christoffel |
| 4,198,961 A | 4/1980 | Arkans |

(Continued)

FOREIGN PATENT DOCUMENTS

| CA | 2601496 | 3/2008 |
|---|---|---|
| EP | 1990039 | 11/2008 |

(Continued)

OTHER PUBLICATIONS

Orthofix International, "Orthofix International Introduces FUSION Lateral OA Brace With New Low-Profile Hinge," News Blaze, published Dec. 4, 2009, http://newsblaze.com/story/20091204050521000002.bw/topstory.html.

(Continued)

*Primary Examiner* — Linda Dvorak
*Assistant Examiner* — Jared W Pike
(74) *Attorney, Agent, or Firm* — K&L Gates LLP

(57) ABSTRACT

A cold therapy system includes a cooling bath; a therapy pad; a heat exchanger; a first pathway fluidly connecting the cooling bath to the heat exchanger; a second pathway fluidly connecting the heat exchanger to an inlet of the therapy pad; a third pathway fluidly connecting an outlet of the therapy pad to the heat exchanger; and a fourth pathway fluidly connecting an outlet of the heat exchanger to the cooling bath.

24 Claims, 11 Drawing Sheets

(56) References Cited

U.S. PATENT DOCUMENTS

| | | |
|---|---|---|
| 4,202,325 A | 5/1980 | Villari et al. |
| 4,206,751 A | 6/1980 | Schneider |
| 4,207,875 A | 6/1980 | Arkans |
| 4,253,449 A | 3/1981 | Arkans et al. |
| 4,306,747 A | 12/1981 | Moss |
| 4,311,135 A | 1/1982 | Brueckner et al. |
| 4,370,975 A | 2/1983 | Wright |
| 4,375,217 A | 3/1983 | Arkans |
| 4,396,010 A | 8/1983 | Arkans |
| 4,453,538 A | 6/1984 | Whitney |
| 4,501,126 A | 2/1985 | Norton |
| 4,694,521 A | 9/1987 | Tominaga |
| 4,773,494 A | 9/1988 | Anderson |
| 4,821,354 A | 4/1989 | Little |
| 4,841,956 A | 6/1989 | Gardner et al. |
| 4,844,072 A | 7/1989 | French et al. |
| 4,966,145 A | 10/1990 | Kikumoto et al. |
| 5,022,387 A | 6/1991 | Hasty |
| 5,109,832 A | 5/1992 | Proctor et al. |
| 5,186,163 A | 2/1993 | Dye |
| 5,218,954 A | 6/1993 | van Bemmelen |
| 5,241,951 A | 9/1993 | Mason et al. |
| 5,241,958 A | 9/1993 | Noeldner |
| 5,261,482 A | 11/1993 | Lomax et al. |
| 5,263,473 A | 11/1993 | McWhorter |
| 5,330,519 A | 7/1994 | Mason et al. |
| 5,383,894 A | 1/1995 | Dye |
| 5,496,262 A | 3/1996 | Johnson, Jr. et al. |
| 5,588,955 A | 12/1996 | Johnson, Jr. et al. |
| 5,626,556 A | 5/1997 | Tobler et al. |
| 5,647,051 A | 7/1997 | Neer |
| 5,669,872 A | 9/1997 | Fox |
| 5,843,007 A | 12/1998 | McEwen et al. |
| 5,865,841 A | 2/1999 | Kolen et al. |
| 5,951,502 A | 9/1999 | Peeler et al. |
| 5,980,561 A | 11/1999 | Kolen et al. |
| 5,989,285 A | 11/1999 | DeVilbiss et al. |
| 6,007,559 A | 12/1999 | Arkans |
| 6,080,120 A | 6/2000 | Sandman et al. |
| 6,129,688 A | 10/2000 | Arkans |
| 6,146,411 A * | 11/2000 | Noda et al. .................... 607/105 |
| 6,290,662 B1 | 9/2001 | Morris et al. |
| 6,296,617 B1 | 10/2001 | Peeler et al. |
| 6,358,219 B1 | 3/2002 | Arkans |
| 6,387,065 B1 | 5/2002 | Tumey |
| 6,436,064 B1 | 8/2002 | Kloecker |
| 6,440,093 B1 | 8/2002 | McEwen et al. |
| 6,447,467 B1 | 9/2002 | Barak |
| 6,463,612 B1 | 10/2002 | Potter |
| 6,463,934 B1 | 10/2002 | Johnson, Jr. et al. |
| 6,478,757 B1 | 11/2002 | Barak |
| 6,494,852 B1 | 12/2002 | Barak et al. |
| 6,544,202 B2 | 4/2003 | McEwen et al. |
| 6,589,194 B1 | 7/2003 | Calderon et al. |
| 6,592,534 B1 | 7/2003 | Rutt et al. |
| 6,685,661 B2 | 2/2004 | Peled |
| 7,044,924 B1 | 5/2006 | Roth et al. |
| 7,063,676 B2 | 6/2006 | Barak et al. |
| 7,191,798 B2 | 3/2007 | Edelman et al. |
| 7,207,959 B1 | 4/2007 | Chandran |
| 7,211,104 B2 | 5/2007 | Edelman |
| 7,282,038 B2 | 10/2007 | Gillis et al. |
| 7,354,410 B2 | 4/2008 | Perry et al. |
| 7,354,411 B2 | 4/2008 | Perry et al. |
| 7,637,879 B2 | 12/2009 | Barak et al. |
| 7,641,623 B2 | 1/2010 | Biondo et al. |
| 7,658,205 B1 | 2/2010 | Edelman et al. |
| 7,694,693 B1 | 4/2010 | Edelman et al. |
| 7,708,707 B2 | 5/2010 | Cook et al. |
| 7,819,829 B1 | 10/2010 | Chandran |
| 7,862,525 B2 | 1/2011 | Carkner et al. |
| 7,871,387 B2 | 1/2011 | Tordella et al. |
| 7,896,823 B2 | 3/2011 | Mangrum et al. |
| 7,909,783 B2 | 3/2011 | Mayer et al. |
| 7,909,861 B2 | 3/2011 | Balachandran et al. |
| 7,931,606 B2 | 4/2011 | Meyer |
| 7,942,838 B2 | 5/2011 | Farrow |
| 7,959,588 B1 | 6/2011 | Wolpa |
| 7,967,766 B2 | 6/2011 | Ravikumar |
| 2001/0039439 A1 * | 11/2001 | Elkins et al. .................... 607/104 |
| 2008/0058911 A1 | 3/2008 | Parish et al. |
| 2008/0077063 A1 | 3/2008 | Meyer et al. |
| 2009/0069731 A1 | 3/2009 | Parish et al. |
| 2009/0124944 A1 | 5/2009 | Ravikumar |
| 2009/0293887 A1 | 12/2009 | Wilkes et al. |
| 2009/0299249 A1 | 12/2009 | Wilkes et al. |
| 2009/0299255 A1 | 12/2009 | Kazala et al. |
| 2009/0299256 A1 | 12/2009 | Barta |
| 2009/0299257 A1 | 12/2009 | Long et al. |
| 2009/0299307 A1 | 12/2009 | Barta et al. |
| 2009/0299308 A1 | 12/2009 | Kazala et al. |
| 2009/0299340 A1 | 12/2009 | Kazala et al. |
| 2009/0299341 A1 | 12/2009 | Kazala et al. |
| 2009/0299342 A1 | 12/2009 | Cavanaugh et al. |
| 2010/0030306 A1 | 2/2010 | Edelman et al. |
| 2010/0100017 A1 | 4/2010 | Maguina |
| 2010/0106229 A1 | 4/2010 | Gammons et al. |
| 2010/0137764 A1 | 6/2010 | Eddy |
| 2010/0210982 A1 | 8/2010 | Balachandran et al. |
| 2010/0249679 A1 | 9/2010 | Perry et al. |
| 2011/0015587 A1 | 1/2011 | Tumey et al. |
| 2011/0015589 A1 | 1/2011 | Svedman et al. |
| 2011/0015590 A1 | 1/2011 | Svedman et al. |
| 2011/0015593 A1 | 1/2011 | Svedman et al. |
| 2011/0077723 A1 | 3/2011 | Parish et al. |
| 2011/0082401 A1 | 4/2011 | Iker et al. |
| 2011/0092927 A1 | 4/2011 | Wilkes et al. |
| 2011/0093050 A1 | 4/2011 | Damkoehler |
| 2011/0152796 A1 | 6/2011 | Kazala, Jr. et al. |
| 2011/0166480 A1 | 7/2011 | Mayer et al. |
| 2011/0178481 A1 | 7/2011 | Locke et al. |
| 2011/0190675 A1 | 8/2011 | Vess |
| 2011/0196269 A1 | 8/2011 | Arkans |
| 2011/0257573 A1 | 10/2011 | Hong et al. |
| 2011/0275983 A1 | 11/2011 | Quisenberry et al. |

FOREIGN PATENT DOCUMENTS

| | | |
|---|---|---|
| EP | 2275165 | 1/2011 |
| FR | 2696342 A3 | 4/1994 |
| GB | 2465712 A | 2/2009 |
| IE | 950163 | 12/1995 |
| WO | 2005/037154 A1 | 4/2005 |
| WO | WO2009/158131 | 12/2009 |
| WO | WO2011/090986 | 7/2011 |

OTHER PUBLICATIONS

Breg Incorporated, "Fusion OA," published 2009, http://www.breg.com/knee-bracing/oa/fusion-oa.html.

Bledsoe Brace Systems, "Bledsoe Cold Control," published 2008, http://bledsoebrace.com/products/cold_control.asp.

International Preliminary Report on Patentability issued Mar. 15, 2013, for related Intl. Appln. No. PCT/US2011/065517.

* cited by examiner

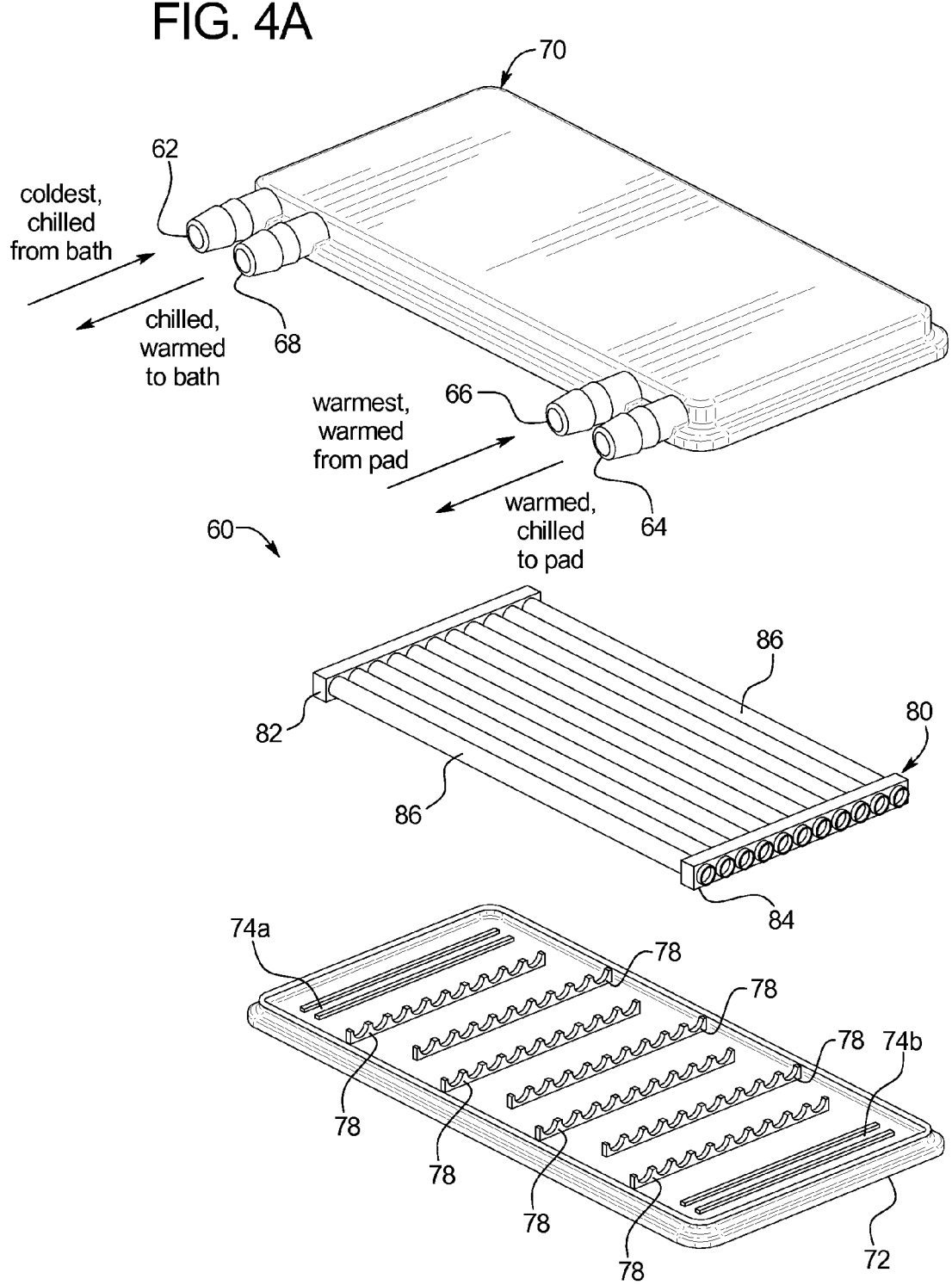

COLD THERAPY APPARATUS USING HEAT EXCHANGER

BACKGROUND

The present disclosure relates generally to orthopedics and in particular to the therapeutic cooling or heating of a sore or injured body part.

It is known to use chilled water to cool and sooth a sore or injured body part. For example, U.S. Pat. Nos. 5,241,951 and 5,330,519 describe a cold therapy unit that uses chilled water. The patents call for a variable flow restrictor for temperature control. The more the flow restrictor is restricted, the less water flows through the cooling pad, resulting in a higher therapy pad temperature. The less the flow restrictor is restricted, the more water flows through the cooling pad, resulting in a lower therapy pad temperature.

While known devices have provided therapeutic cooling, the devices have had certain drawbacks. For instance, temperature control for certain of these devices has been difficult, leading to instances in which water has been chilled to a level that is uncomfortable for the patient. Also, certain devices cause the ice to melt too quickly, expending the thermal potential of the device. Second, it is desirable to ensure that the water delivered to the cooling pad is not uncomfortably cold.

SUMMARY

The present disclosure sets forth multiple primary embodiments, each of which uses a heat exchanger that recoups some of the heat imparted to the cooling water by the user's body. The heat exchanger receives chilled water from a cooling bath and passes the chilled water through a chilled water pathway of the heat exchanger. The heat exchanger also receives warmed water from a therapy pad placed physically on the user and passes the warmed water through a warmed water pathway of the heat exchanger. The outlet of the chilled water pathway leads to the therapy pad. The outlet of the warmed water pathway leads to the cooling bath.

In one embodiment, the heat exchanger is a shell and tube type heat exchanger. The chilled fluid from the cooling bath can run through the insides of the tubes, while the warmed fluid returning from the therapy pad flows over the outsides of the tubes. Alternatively, the warmed fluid returning from the therapy pad runs through the insides of the tubes, while the chilled fluid from the cooling bath flows over the outsides of the tubes. The shells define a tube inlet manifold and a tube outlet manifold. The tubes are connected to the inlet and outlet manifolds. The tubes in one embodiment run a single pass between the inlet and outlet manifolds. Alternatively, the tubes can run multiple passes between the manifolds, such that one of the manifolds can connect to both the inlet and outlet to the tube sides of the heat exchanger.

In one embodiment, the shell includes a base and cover made of a thermally insulating plastic. The tubes can be metal, such as copper or aluminum. The inlet and outlet manifold walls can also be made of copper or aluminum, respectively. Alternatively, the tubes and manifold walls are plastic, such as a thin-walled plastic tubing. In any case, the tubes can be welded to the inlet and outlet of the manifold walls. The manifold walls slide into the shell base, the shell cover sealing the manifold walls into place against the shell base. All fluid inlets and outlets to the shell are located on one of the shell pieces in one embodiment, such as the shell base.

In another embodiment, the heat exchanger includes abutting tubular or welded flow path warm and chilled fluid lines. The chilled and warmed fluid pathways or lumens can be run together in an X-Y plane. Alternatively, the chilled and warmed fluid pathways each meander in an X-Y plane but be spaced from each other in a Z or elevational direction. In either case, it is contemplated to make the heat exchanger a flexible pad that either forms the fluid pathways via seals in the pad sheeting or seals flexible tubing within the pad sheeting. In an embodiment, the heat exchanger is made of the same sheeting material as is the therapy pad.

In a further embodiment, the system can employ more than one heat exchanger in series to achieve warmer temperatures and higher flow rates. As described herein, the system may employ a valve that allows the user to vary temperature at the therapy pad. The multiple, in series heat exchangers can be particularly useful for creating warmer temperatures for the system using a temperature varying valve discussed in detail below.

Any of the heat exchanger configurations can be made in a co-current flow arrangement that places the warmest fluid returning from the patient into thermal communication with the coldest fluid from the cooling bath. The chilled fluid pathway runs along the warmed fluid pathway in, for example, a serpentine bending and/or twisting manner, such that the cooled-down warmed fluid exits the heat exchanger with the warmed-up chilled fluid. The heat exchangers in another embodiment are a counter-current heat exchangers, in which the coldest chilled fluid from the cooling bath meets the cooled-down, warmed fluid. The chilled fluid pathway runs along the warmed fluid pathway in, for example, a serpentine bending and/or twisting manner such that the warmed-up, chilled fluid exits the heat exchanger meeting the warmest warm fluid from the therapy pad.

In one embodiment, the heat exchanger is located outside of the cooling bathwater. For example, the heat exchanger can be located in the lid of, be hung from or otherwise be affixed to the outside of the cooling bath. A pump submerged the cooling bath pumps chilled fluid into the heat exchanger. The chilled fluid is heated by fluid in the heat exchanger returning from the therapy pad. The chilled fluid flows from the heat exchanger into the therapy pad and absorbs additional heat from the user's body. The pumped fluid then flows from the therapy pad to the heat exchanger where it delivers heat to the chilled fluid flowing through the heat exchanger. The pumped fluid then flows from the heat exchanger to the cooling bath and the cycle is repeated.

In one embodiment, the heat exchanger is located inside the lid of the cooling bath. The heat exchanger is connected to the pump by the outlet tube from the pump, which is kept relatively short. The pump is connected to or pulled taught against a standoff extending down from the heat exchanger lid. The standoff positions the pump inside the water/ice of the cooling bath at a desired depth. A bath return line extends from the heat exchanger to the water/ice in the bath. To- and from-therapy pad lines extend from the heat exchanger out of the lid to the therapy pad. As described in detail below, the cold therapy system can provide a diverter valve for temperature control. If so a return line bypassing the heat exchanger is provided and runs from the valve, through the sleeve, to the cooling bath. The heat exchanger is alternatively submerged in the cooling bath. Here, the warmed fluid is still supplied from the thermal pad. The heat exchanger in this case can be affixed to an inner wall of the cooling bath, but at a level that is submerged in the cooled ice water.

In a first primary embodiment, a fixed fluid restrictor can be placed in the warmer water return line, for example, between the heat exchanger and the therapy pad. The fixed fluid restrictor is optimized to provide a desired fluid temperature in the therapy pad, e.g., 46° F. (7.8° C.), assuming an average fluid temperature in the cooling bath of e.g., 32° F. (0° C.) to 34° F. (1.1° C.), an average heat transfer from the patient and a pump flowrate of about 250 milliliters ("ml") per minute. In this first primary embodiment, the user does not adjust a valve or other control to adjust the temperature. The user can however vary the amount of ice or other cooling mechanism that is placed in the cooling bath, e.g., a frozen gel pack or multiple ones of same. A readout, e.g., a digital light-emitting diode ("LED") or liquid crystal display ("LCD") readout is provided to inform the user of the temperature of the fluid flowing through the therapy pad.

In a second primary embodiment, a valve is added to the first primary embodiment. The valve in one implementation is a diverter valve and is manually operated. The diverter valve is placed in one embodiment downstream in a leg of a line teed off of the warmed fluid return line from the therapy pad. That is, the warmed fluid return line splits, with one branch running to the heat exchanger and a second branch by-passing the heat exchanger and running directly to the cooling bath. The diverter valve can alternatively be placed in either the heat exchanger or by-pass branches off of the warmed fluid return line. The first branch running to the heat exchanger flows through the heat exchanger as described above and flows from the heat exchanger to the cooling bath. Thus all fluid returning from therapy pad flows eventually to the cooling bath, but a portion of the fluid does so via the heat exchanger while the remaining portion does so directly. In this manner, flowrate is not effected by the valve position.

The diverter valve creates a variable restriction. In the configuration in which the diverter valve is located in the branch returning to the cooling bath, the more open the diverter valve, the more fluid flow through it, and the less fluid through the other, heat exchanger branch. The less open the diverter valve, the less fluid flows through the valve and the more fluid flows through the other branch.

As discussed, the diverter valve is in one implementation placed in the warmed fluid branch running directly to the cooling bath. Here, when the user opens the diverter valve, more fluid flows directly to the cooling bath, while less fluid flows the heat exchanger to gather heat, resulting in an overall decrease in temperature of the chilled fluid flowing to the therapy pad. In the reverse, when the user closes the diverter valve, less return fluid flows directly to the cooling bath, while more return fluid flows through the heat exchanger to gather heat, resulting in an overall increase in temperature of the chilled fluid flowing to the therapy pad. Here, a visual cue provided to the user to indicate the way to actuate a control to decrease therapy pad temperature corresponds to an opening of the diverter valve. And, the visual cue provided to the user to indicate the way to actuate a control to increase therapy pad temperature corresponds to a closing of the diverter valve.

It should be appreciated, and as described in detail below, that if the diverter valve is placed instead in the warmed fluid branch running to the heat exchanger, that the visual cue provided to the user to indicate the way to actuate a control to increase therapy pad temperature corresponds to an opening of the diverter valve. Here, opening the diverter valve allows more fluid to flow to the heat exchanger, increasing therapy pad temperature. Closing the diverter valve increases back pressure, pushing more fluid directly to the cooling bath.

It is accordingly an advantage of the present disclosure to provide a cold therapy unit with improved therapy pad temperature control.

It is another advantage of the present disclosure to provide a cold therapy unit that cools the user safely.

It is a further advantage of the present disclosure to provide a cold therapy unit that efficiently and effectively incorporates a heat exchanger that exchanges heat from fluid warmed by the patient.

Additional features and advantages are described herein, and will be apparent from the following Detailed Description and the figures.

BRIEF DESCRIPTION OF THE FIGURES

FIG. 4A is an exploded perspective view of one embodiment of a heat exchanger used with any of the cold therapy systems of the present disclosure.

DETAILED DESCRIPTION

Flow Regimes

Figure 1:
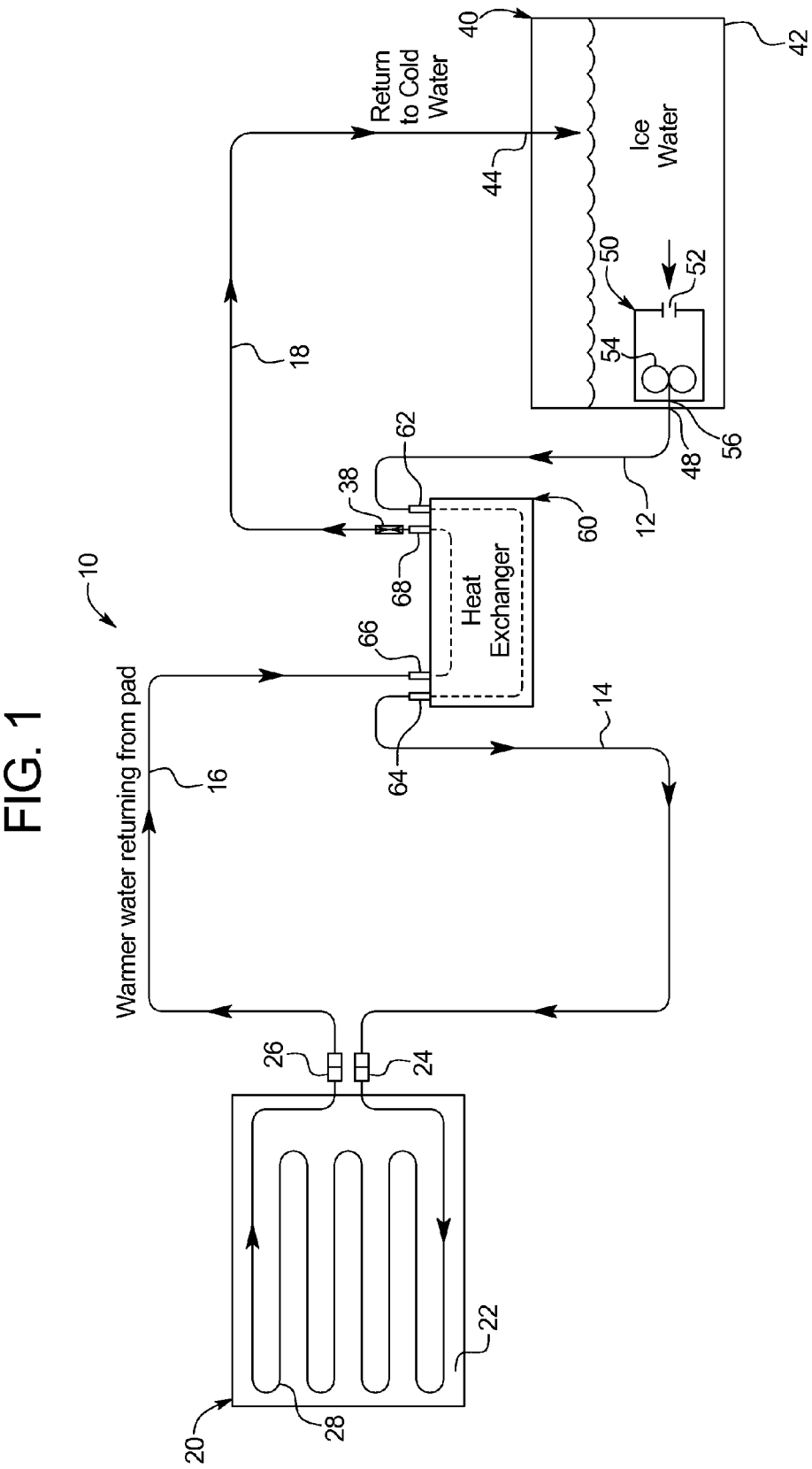
FIG. 1 is a schematic view of one embodiment of a cold therapy system of the present disclosure.

Referring now to the drawings and in particular to FIG. 1, one embodiment of a cold therapy system of the present disclosure is illustrated by System 10. Primary components of System 10 include a therapy pad 20, a cooling bath 40 and a heat exchanger 60. Each of these items is discussed in detail below. There are a number of passageways that link therapy pad 20, cooling bath 40 and heat exchanger 60. For instance, a bath-exchanger pathway 12 extends from a bath outlet 48 of cooling bath 40 to a chilled water inlet 62 of heat exchanger 60. An exchanger-pad pathway 14 extends from chilled water outlet 64 of heat exchanger 60 to a pad inlet connector 24 of patient pad 20. A pad-exchanger pathway 16 extends from pad outlet connector 26 to heated water inlet 66 of heat exchanger 60. An exchanger-bath pathway 18 extends from a heated water outlet 68 of heat exchanger 60 to a heat exchanger return inlet 44 of cooling bath 40.

Figure 3:
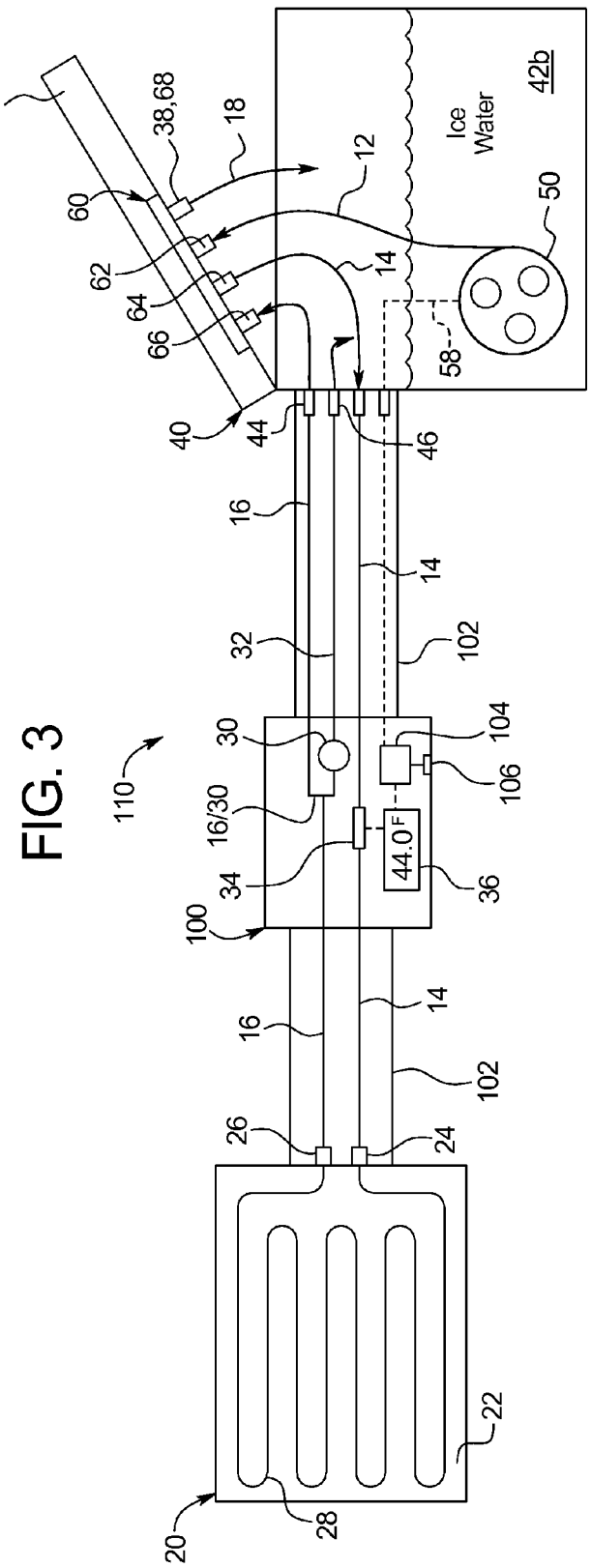
FIG. 3 is a schematic elevation view of the cold therapy system of FIG. 2 showing one embodiment (for any of the systems herein) for routing the pathway tubing, for locating controls and electronics, and for mounting the heat exchanger.

In an embodiment, each of pathways 12 to 18 is a tube, such as a ¼ inch (6.4 millimeters ("mm")), 5/16 inch (7.9 mm), or 3/8 inch (9.5 mm) outer diameter tube, which can be made of silicon, polyvinyl chloride or other tube. In one preferred embodiment, tubing for pathways 12 to 18 is polypropylene tubing, having for example, a 0.156 inch (4.00 mm) outside diameter and a wall thickness of 0.005 inch (127 mm). As discussed in detail below, heat exchanger 60 in one embodiment is mounted to the inside of cooling bath 40. Here, pathways 12 and 18 can still be any of the tubing embodiments discussed above or alternatively be fluid pathways formed, at least in part, integrally in the wall or walls of housing 42 of cooling bath 40. Further, while pathways 14 and 16 are shown in FIG. 1 as extending away from each other for clarity, it is contemplated as seen in FIG. 3 to route both pathways 14 and 16 inside of a single routing sleeve, such as an insulating sleeve made of, for example, extruded polyurethane foam. The routing sleeve enables the user or patient to easily maneuver passageways 14 and 16 and place therapy pad 20 at a desired location on the patient's body.

Therapy pad 20 includes a patient wrap 22, which in an embodiment is a multi-ply structure made of, for example, polyurethane film that is left plain on one side and polyurethane film with a hook engageable pile surface bonded to the other side. Wrap 22 can include ears or tabs having mating pile and hook sections that enable pad 20 to be removeably secured to an area of the user's body. The multiple plies of patient wrap 22 are welded together along their peripheral edges and also to secure a patient cooling pathway 28 that extends from pad inlet connector 24 to pad outlet connector 26. In an embodiment, patient cooling pathway 28 is a serpentine section of tubing, such as the tubing for passageways 14 and 16. Alternatively, patient cooling pathway 28 is a serpentine pattern welded via the multiple plies of patient wrap 22, so as to communicate fluidly with path inlet connector 24 and pad outlet connector 26. In any case, chilled fluid from cooling bath 40 and heat exchanger 60 flows through pad inlet connector 24, through patient cooling pathway 28 to thereby cool the patient and absorb heat from the patient, through pad outlet connector 26, through heat exchanger 60 and returning to cooling bath 40.

Cooling bath 40 includes a housing 42 that is made of a thermally insulating plastic. Housing 42 can have an inner shell made for example from a dishwasher safe polypropylene plastic, and an outer shell and a lid both made from medium density polyethylene. Housing 42 in an embodiment includes a hinged or otherwise removable lid, which allows access to the inside of housing 42 and cooling bath 40. In an embodiment, housing 42 includes an inner and outer shell, which separates an insulating area that can either be evacuated or filled with an insulating material, such as an insulating foam, e.g., polyurethane insulation foamed in place or a sheet insulation such as Thinsulate™. Further alternatively, air between the inner and outer shells serves as an insulator.

A liquid pump 50 is placed within bath housing 42 of cooling bath 40 and in an embodiment is allowed to either rest on the bottom of bath housing 42 or alternatively to be removeably secured to the bottom or lower portion of one of the side walls of bath housing 42. In any case, liquid pump 50 is configured to be submerged beneath a volume of ice water that is filled within bath housing 42. Liquid pump 50 includes a pump inlet 52, a pump motor 54 and a pump outlet 56. In an embodiment, pump motor 54 outputs water pulled in from inlet 52 through outlet 56 at a pressure of about 9.0 psig and a flowrate of 250 ml per minute. Pump 50 may pump up to 1500 ml per minute at about 4.5 psig.

In the illustrated embodiment, pump outlet 56 communicates fluidly with bath outlet 48, which in turn communicates fluidly with bath-exchanger pathway 12 running to heat exchanger 60. Such arrangement can be used if heat exchanger 60 is located on the outside of bath housing 42. As mentioned earlier, however, it is contemplated to mount heat exchanger 60 within housing 42, in which case pump outlet 56 communicates via bath-exchanger pathway 12 to chilled water inlet 62 of heat exchanger 60 without passing through or communicating with a bath outlet 48. Bath outlet 48 is instead configured to communicate with heat exchanger 60. One suitable arrangement for mounting heat exchanger 60 within housing 42 is shown and described in detail below.

In an embodiment, pump motor 54 is powered via house voltage, such as 120 VAC or 240 VAC, or is alternatively fed via a power supply, such as a direct current power supply shown in detail below. Pump motor 54 includes a hermetically sealed power connection. A water-proof power cord is run in one embodiment from pump motor 54 to either an electrical port located on the outside of bath housing 42 or alternatively through the insulating sleeve holding pathways 14 and 16, from a location at which a power cord electrical port is provided, e.g., at a control unit illustrated below.

In the illustrated embodiment, a fixed restrictor 38 is placed in exchanger-bath pathway 18 just downstream of warmed water outlet 68 of heat exchanger 60. Fixed restrictor 38 can be a reduced diameter union or section of tubing that creates a back-pressure in pad-exchanger pathway 16 and accordingly in the patient's cooling pathway 28, so as to help inflate patient cooling pathway 28 located within patient wrap 22 of therapy pad 20. In an alternative embodiment, fixed restrictor 38 is placed in pad-exchanger pathway 16 just upstream of warmed water inlet 66 to heat exchanger 60.

Liquid pump 50 pumps ice water from bath housing 42 through bath-exchanger pathway 12 into the cooling section or compartment of heat exchanger 60. The ice water accumulates heat from the warmed water returning from therapy pad 20 through pad-exchanger pathway 16. Slightly heated chilled water than exits heat exchanger 60 via chilled water outlet 64 and flows through exchanger-pad pathway 14 into therapy pad 20. The slightly warmed-up chilled water flowing through patient cooling pathway 28 of therapy pad 20, inflated via restrictor 38, cools the patient, absorbing heat from the patient, and exits pad outlet connector 26 as warmed water.

The warmed water flows through pad-exchanger pathway 16 and into heat exchanger 60 via warmed water inlet 66, and into a warmed fluid section or compartment of heat exchanger 60. The warmed fluid heats the chilled fluid from bath 40 flowing through the chilled section or compartment of heat exchanger 60, such that warmed fluid entering through inlet 66 is cooled slightly before leaving warmed water outlet 68 and flowing through exchanger-bath pathway 18 and heat exchanger return inlet 44 of bath housing 42 into the ice water of cooling bath 40. The cycle just described is run continuously and for as long as the user desires and/or there is a temperature gradient between therapy pad 20 and cooling bath 40.

In the embodiment of system 10, the patient is not required to make and is provided with no ability to make temperature adjustments other than to vary an amount of ice and/or water placed in bath housing 42 of cooling bath 40 and to adjust the position of therapy pad 20. Fixed restrictor 38 is again fixed and thus does not provide a user with the ability for temperature variability.

Figure 2:
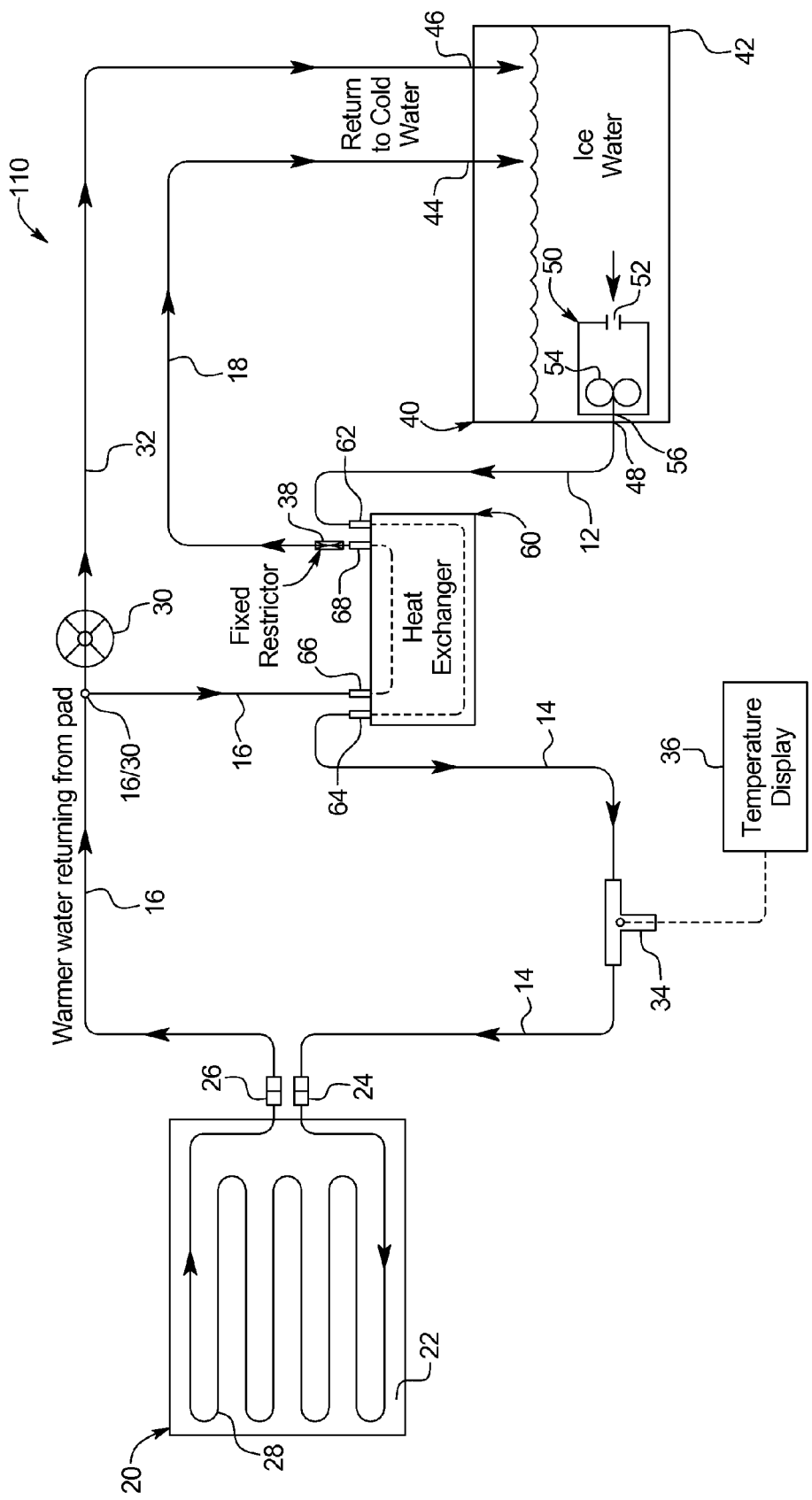
FIG. 2 is a schematic view of a second embodiment of the cold therapy system of the present disclosure.

Referring now to FIG. 2, system 110 is illustrated and does provide the user with an ability to vary the temperature of the fluid flowing through patient cooling pathway 28 of therapy pad 20. System 110 also adds a temperature sensor 34 and a temperature display 36, which can also be provided with the system 10 if desired. Temperature sensor 34 can be a thermistor or thermocouple, which outputs a voltage to a digital light-emitting diode ("LED") display or liquid crystal display ("LCD"). As discussed above, in one embodiment the hermetically sealed power wires from liquid pump 50 run through the insulating sleeve surrounding pathways 14 and 16. It is contemplated to terminate the power wires at a patient control station that houses temperature probe 34 and temperature display 36. FIG. 3 below illustrates one embodiment in which the manual control for diverter valve 30 is also located with a temperature display 36 and temperature sensor 34.

The primary difference between system 110 of FIG. 2 and system 10 of FIG. 1 is the provision of diverter valve 30 and a diverter-bath or bypass branch 32 extending in parallel with exchanger-bath pathway 18 to cooling bath 40. In the illustrated embodiment, diverter-bath branch 32 communicates fluidly with the inside of bath housing 42 via a direct return inlet 46. As seen in FIG. 2, pad-exchanger pathway 16 tees at tee 16/30 into a first branch 16 that follows the same path as pad-exchanger pathway 16 of system 10. A second branch from tee 16/30 flows through diverter-bath pathway or bypass branch 32 via diverter valve 30 directly into bath housing 40, bypassing heat exchanger 60. It should be appreciated that water returning through bypass branch 32 is warmer than water returning to bath housing 42 via exchange-bath pathway 18. Water returning to bath housing 42 via bypass branch 32 does not give up heat in heat exchanger 60.

In an embodiment, diverter valve 30 is a two-way restricting valve that either opens or closes flow to bypass return branch 32 depending on which way the user or patient turns a dial or knob associated with diverter valve 30. In the configuration of system 110 shown in FIG. 2, the more the user or patient opens valve 30, the more fluid flows through bypass return branch 32, robbing fluid from pad-exchanger branch 16, which (i) reduces an amount of warming fluid flowing to heat exchanger 60 and (ii) reduces an overall collective fluid temperature of fluid delivered to bath housing 42. Both (i) and (ii) result in an overall cooler flow of fluid through exchanger-pad pathway 14 and thus an overall cooler fluid flowing through patient cooling pathway 28 of therapy pad 20. Conversely, when the patient closes diverter valve 30, less water returns directly to bath housing 42 via bypass branch 32 and (ii) more warmed fluid is forced via pad-exchanger branch 16 through the heating side or compartment of heat exchanger 60. Both (i) and (ii) here result in an overall increased temperature through exchanger-pad pathway 14 and an overall warmer temperature of fluid flowing through patient cooling pathway 28 of therapy pad 20.

It should be appreciated that regardless of the setting of diverter valve 30, the overall flowrate of water returning to bath housing 42 via return branches 18 and 32 does not collectively vary. In illustrated embodiment 110, fixed restrictor 38 is again placed directly downstream of warmed water outlet 68 of heat exchanger 60 to inflate therapy pad 20. As before, it is contemplated to place fixed restrictor 38 in pad-exchanger pathway 16 just upstream of warmed water inlet 66 of heat exchanger 60 in an alternative embodiment. In either case, however, the fixed nature of restrictor 38 sets an overall flowrate through the entire system 110 that is otherwise not varied by the setting of diverter valve 30.

In another alternative embodiment, diverter valve 30 can be placed instead in pad-exchanger branch 16 downstream of tee 16/30. In this alternative configuration, the operation of diverter valve 30 works oppositely from that described above. Namely, as the patient opens diverter valve 30, more fluid flows through pad-exchanger branch 16 and thus through heat exchanger 60, while less fluid flows through bypass return branch 32. The result here is to create an overall warmer temperature at patient cooling pathway 28 of therapy pad 20. Conversely, when a patient or user closes valve 30, more fluid is shunted through bypass return branch 32, less fluid flows through heat exchanger 60, resulting in an overall lower temperature at therapy pad 22.

In still another alternative embodiment, tee 16/30 is replaced with a three-way valve (not illustrated). Here, the manual manipulation of the valve 30 proportions an amount of water returning through bypass branch 32 versus pad-exchanger branch 16. As the three-way valve closes pad-exchanger branch 16, more fluid flows through bypass branch 32, resulting in an overall cooling of fluid flowing through therapy pad 20. Conversely, when the user closes branch 32, more fluid flows through heat exchanger branch 16, resulting in an overall warmer fluid flowing through therapy pad 20.

Referring now to FIG. 3, system 110 is illustrated schematically to show one configuration for mounting heat exchanger 60 and to also show how the various hydraulic and electrical lines can be run through a single control station 100 via a single insulating sleeve 102. Sleeve 102 runs from cooling bath 40 to therapy pad 20, interrupted by control station 100 in the illustrated embodiment. FIG. 3 illustrates that in one embodiment, heat exchanger 60 is inserted into the underside of a lid 42a hinged to a base 42b of bath housing 42. Here, bath-exchanger pathway 12 and exchanger-bath pathway 18 are completely internal lines housed ergonomically within bath housing 42. Exchanger-pad pathway 14 begins inside bath housing 42 and extends out of the housing within insulating sleeve 102 and control station 100. Exchanger-pad pathway communicates with temperature sensor 34 and extends to pad inlet connector 24 of therapy pad 20.

An electrical line 58 extends from pump 50, through insulating sleeve 102, to a power supply 104, such as a twenty-four VDC power supply. In the illustrated embodiment, power supply 104 powers both liquid pump 50 and temperature display 36 with the same voltage. An alternating current plug 106 powers the inlet side of power supply 104 and accepts a power cord running to the patient's house power. Pad-exchanger branch 16 returning from therapy pad 20 extends through insulating sleeve 102 into control station 100 and tee 16/30, which splits into (i) heat exchanger branch 16, running to warmed water inlet 66 of heat exchanger 60 via a heat exchanger return inlet 44 of bath housing 42, and (ii) bypass branch 32 via diverter valve 30. Bypass return branch 32 extends via insulating sleeve 102 to a direct return inlet 46 at bath housing 42. The manual control for diverter valve 30 is also located at control station 100 as illustrated in FIG. 3.

Once inside bath housing 42, pad-exchanger branch 16 connects to warmed water inlet 66. Heat exchanger-pad pathway 14 extends from chilled water outlet 64 of heat exchanger 60 out of housing 42. Path-exchanger pathway 12 connects to heat exchanger via chilled water inlet 62. In the illustrated embodiment, warmed water outlet 68 doubles as fixed restrictor 38, returning warmed water to the ice-water mixture within cooling bath 40. It should be appreciated that the connectors and lines associated with FIG. 3 are shown schematically are routed within bath housing 42 in an ergonomic and esthetically pleasing manner.

With either system 10 or 110, it is also contemplated to make heat exchanger 60 removable from lid 42a in an embodiment, such that the heat exchanger units can be replaced or repaired if needed. Alternatively, heat exchanger 60 is built as an integral part of lid 42a. Further alternatively, heat exchanger 60 is mounted integrally or removeably in any of the side walls of base 42b of bath housing 42. Still further alternatively, heat exchanger 60 is submerged within the ice-water of bath 40, like pump 50.

Heat Exchangers

Figure 4B:
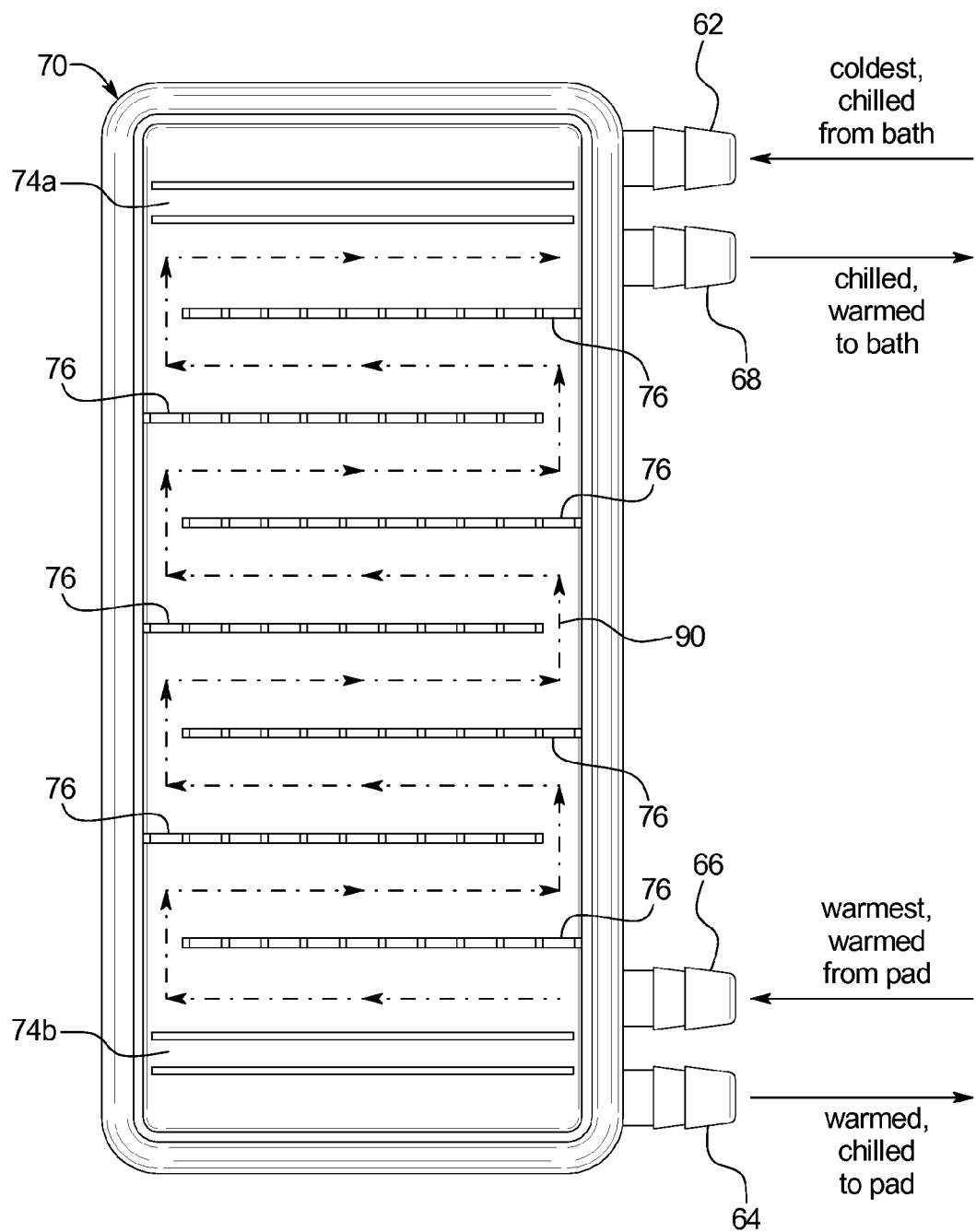
FIG. 4B is a bottom plan view of one embodiment of a shell component of the heat exchanger of FIG. 4A showing a baffled shell flow arrangement.

Referring now to FIGS. 4A and 4B, one embodiment of heat exchanger 60 is illustrated. Here, heat exchanger 60 includes a shell tray 70 and a shell cover 72 that can be welded permanently or fastened and sealed removeably to shell tray 70. A tube bank or bundle 80 is sandwiched between shell tray 70 and shell cover 72. In the illustrated embodiment, the inlets and outlets of shell tray 70 are shown such that the insides of the tubes 86 of tube bank 80 receive chilled fluid from cooling bath 40 (as opposed to the chilled water flowing around the outside of tubes 86). Tube bundle or bank 80 receives chilled fluid from cooling bath 40, while shell tray 70 receives warmed fluid from therapy pad 20. Here, the warmed fluid from therapy pad 20 flows around the outside of tube bank 80, transmitting heat through the walls of tubes 86 to the chilled fluid running through the insides of the tubes 86 of tube bank 80. Alternatively, tube bank 80 receives warmed fluid from therapy pad 20, while shell tray 70 receives chilled fluid from cooling bath 40. In this alternative embodiment, the chilled fluid flows around the outsides of the tubes 86 of tube bank 80 and absorbs heat through the walls of the tubes 86 from warmed fluid flowing through the insides of the tubes.

Shell tray 70 and shell cover 72 each include or define a mating portion of manifold receiving slots or holders 74a and 74b. Manifold 82 of tube bank 80 slides sealingly into the mated manifold holder 74a, while outlet manifold 84 of tube bank 80 slides sealingly into the mated manifold holder 74b. Inlet manifold 82 and outlet manifold 84 are then welded to the raised ridges of the manifold holders 74a and 74b in one embodiment. Alternatively, the pressure applied by shell cover 72 and shell tray 70 when connected together seals inlet manifold 82 and outlet manifold 84 within heat exchanger 60. In the illustrated embodiment, a zone within shell tray 70 leading from chilled water inlet 62 to inlet manifold 82 holds chilled fluid from cooling bath 40. Likewise, a zone leading from a space within shell tray 70 located between outlet manifold 84 and chilled water outlet 64 collects the slightly heated chilled water to be delivered via exchanger-pad pathway 14 to therapy pad 20. Likewise, inlet manifold 82 and outlet manifold 84 trap warmed fluid returning from therapy pad 20 between the manifolds, such that the warmed fluid can flow over tubes 86 of tube bank 80 for a desired heat exchange. Alternatively, as discussed, the fluid returning from therapy pad 20 is flowed into the zones on the outsides of manifolds 82 and 84, while chilled water from cooling bath 40 flows between manifolds 82 and 84.

In the illustrated embodiment, chilled fluid from cooling bath 40 flows left to right in the perspective view of FIG. 4A (top to bottom in FIG. 4B), while warmed fluid flows generally from right to left in FIG. 4A (bottom to top in FIG. 4B), forming a counter-current heat exchanger. A counter-current flow may be desirable especially in a case in which the flowrates may be less than optimal, and when the overall thermal efficiency may depend largely on the thickness of tubes 86 and the water's heat exchange coefficient on either sides of the walls of tubes 86.

As seen in FIG. 4B, shell tray includes or defines tube holding baffle portions 76. Tube holding baffle portions 76 mate with tube holding baffle portions 78 of shell cover (shown in FIG. 4A) to form baffles 76/78 that direct the shell flow in a serpentine pathway 90 from bottom to top as seen in FIG. 4B. Baffles 76/78 decrease cross-sectional fluid flow surface area, increasing fluid flowrate and thus increasing thermal exchange efficiency. Baffles 76/78 also force the shell fluid flow to change direction multiple times, increasing turbulence, which also increases the thermal exchange efficiency. Still further, baffles 76/78 hold tubes 86 (which can be very thin walled) generally centered within shell tray 70 and a shell cover 72, providing a structurally sound dynamic fluid flow system.

Alternatively, heat exchanger 60 can be constructed in a co-current flow arrangement, such that chilled fluid runs in the same general direction through the insides of tubes 86 as does the warmed fluid flowing along the outside of tube 86 (or vice versa with warmed flowing through the insides of tubes 86, while chilled flow is the shell flow). Although not illustrated, either one or both of the insides of tube 86 and the outside shell compartment can be provided with additional tabulators or tabulating media to disrupt the flow of chilled and/or warmed fluid to increase heat exchange efficiency.

In an embodiment, tubes 86 of tube bank 80 are made of thermally conductive material, such as aluminum or copper. Alternatively, it has been found that a thin walled plastic tubing provides adequate heat exchange. For instance, tubes 86 can be plastic polyethylene or polypropylene tubes having a wall thickness of 0.005 inch (0.127 millimeter). In an embodiment, shell trays 70 and shell cover 72 are made of acrylonitrile butadiene styrene ("ABS"). The heat exchanger 60 is welded together in one embodiment, e.g., ultrasonically if plastic or via heated solder if metal. Alternatively, the heat exchanger 60 parts are solvent bonded together. It is contemplated that heat exchanger 60 under any construction can withstand a test pressure of about 12 to about 15 psig and an operating pressure of about 10 psig.

Figure 5:
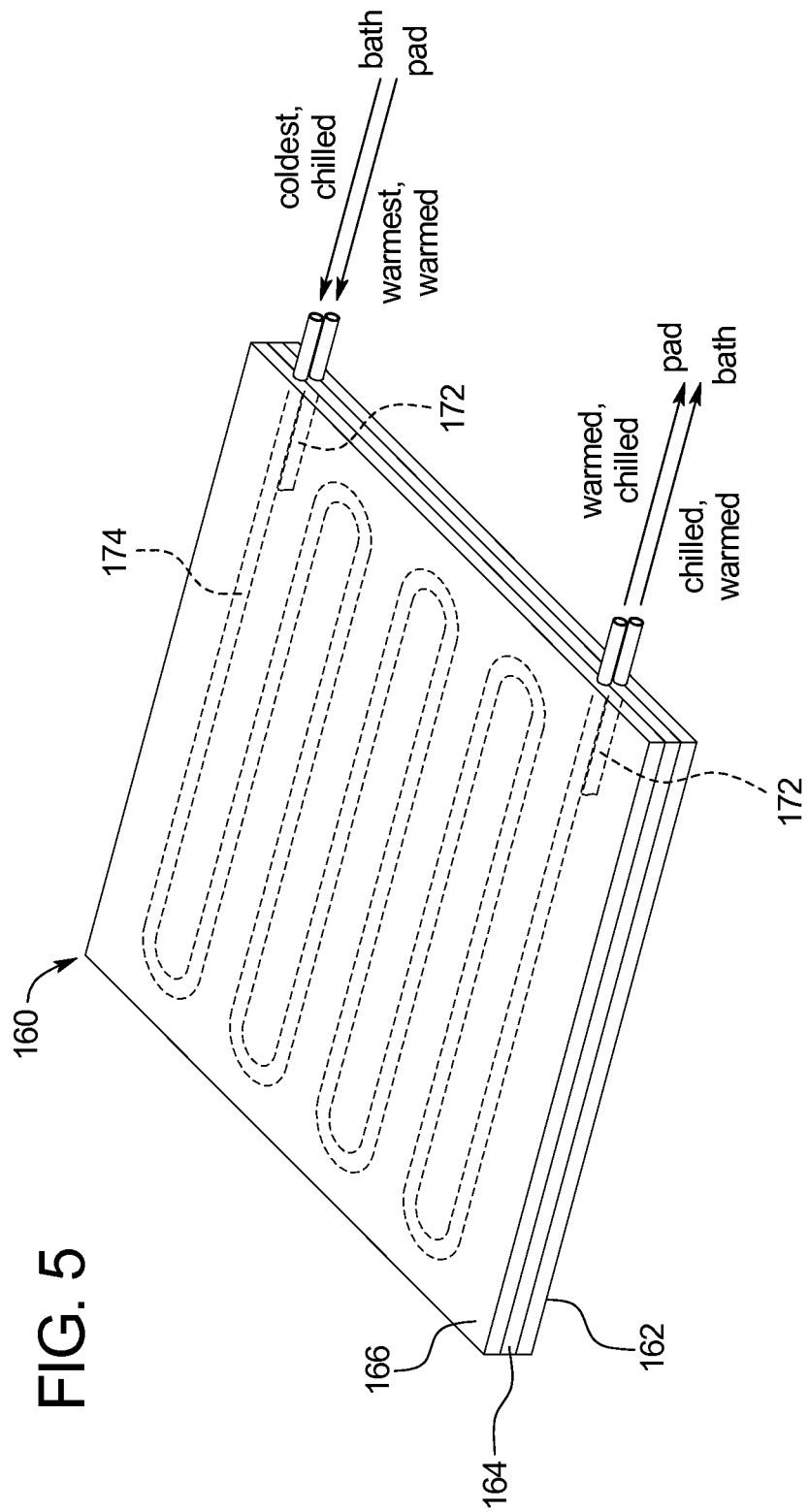
FIG. 5 is a perspective view of one alternative embodiment of a flexible heat exchanger used with any of the cold therapy systems of the present disclosure.

Shell and tube exchanger 60 is one suitable heat exchanger for systems 10 and 110 of the present disclosure. Referring now to FIG. 5, one alternative flexible heat exchanger 160 is illustrated, which can be made for example of the same material as patient wrap 22. Heat exchanger 160 can be used with either system 10 or 100. A three-ply 162, 164, 166 heat exchanger pad can be provided for example, in which the center ply 164 and lower ply 162 are welded to form a serpentine or otherwise winding pathway 172 for one of the chilled and warmed fluids. The center 164 and upper 166 plies form a mirroring serpentine or otherwise winding pathway 174 for the other of the warmed and chilled fluid. The serpentine pathways 172 and 174 run in an X-Y plane and abut each other in a Z-direction.

Alternative flexible heat exchanger 160 can be formed in a counter-current or a co-current flow manner as described above. The illustrated embodiment shows a co-current implementation in which the coldest chilled fluid from bath 40 is inputted into exchanger 160 along with the warmest warmed fluid from therapy pad 20. The flexible alternative heat exchanger can still further alternatively include two flexible plies 162, 166 that trap or hold serpentine chilled and warmed fluid tubes (not illustrated) instead of the welded pathways. The tubes extend again in an X-Y plane and can abut each other in either the X-Y plan or in a Z-direction arrangement. In any case, the flexible alternative heat exchanger can be fixed to the inside or outside of cooling bath 40.

Figure 6:
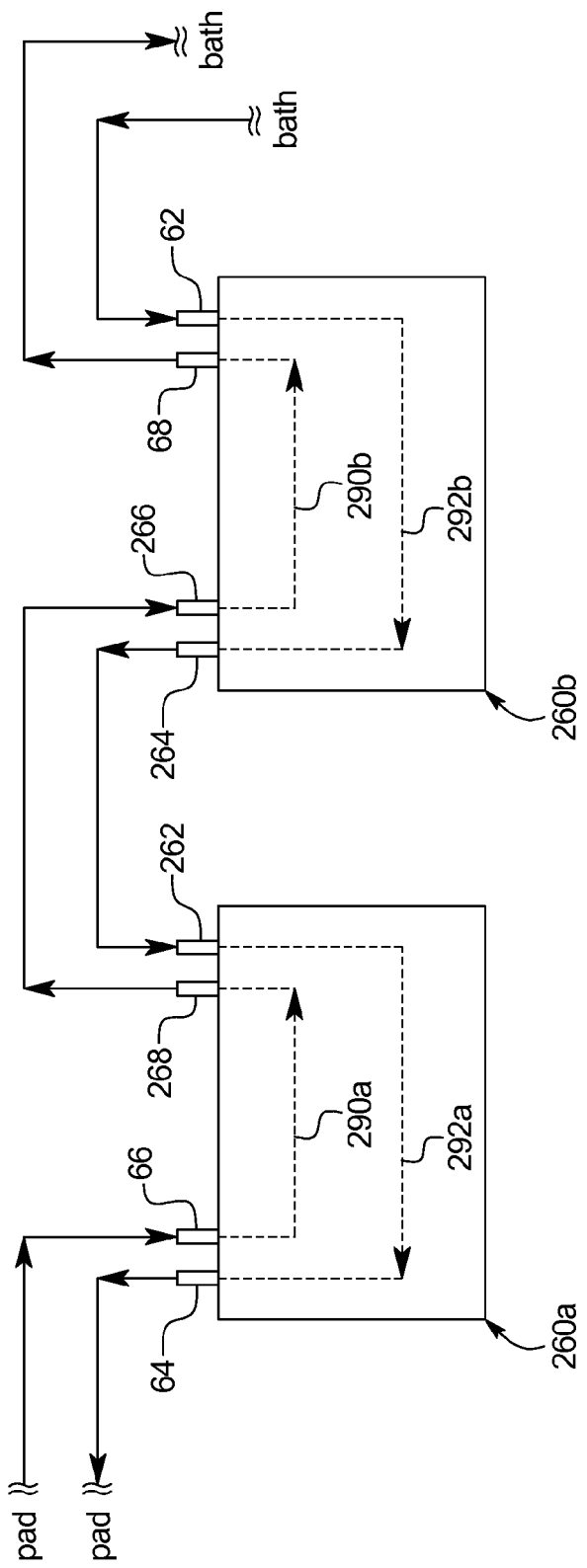
FIG. 6 is a schematic view of one alternative cold therapy flow schematic employing two or more heat exchangers in series.

Referring now to FIG. 6, an alternative dual heat exchanger embodiment is illustrated. First and second heat exchangers 260a and 260b are provided and can be made according to any of the structural heat exchanger types described herein, e.g., of a type like heat exchanger 60 or heat exchanger 160. Multiple heat exchangers, such as two heat exchangers 260a and 260b, can be provided for either fixed restrictor system 10 or variable pad temperature system 110. It is contemplated that heat exchangers 260a and 260b can be smaller relatively inexpensive heat exchangers that each can be mounted conveniently within bath housing 42, but which collectively provide more surface area than single exchangers 60 and 160 above. The advanced heat exchange obtained through dual heat exchangers 260a and 260b may not be as applicable to fixed restrictor 10, which is configured in one embodiment to allow for a Minimum safe therapy pad temperature of 40° F. (4.4 C). In the adjustable pad temperature system 110 on the other hand in which return water can be diverted away from the heat exchanger(s), it may be necessary to provide a higher, more turbulent flowrate through a larger surface area that dual exchangers 260a and 260b provide to maintain the desired allowable minimum pad temperature.

In FIG. 6, chilled water outlet 64 leading to therapy pad 20 and heated water inlet 66 leading from therapy pad 20 are provided on a therapy pad end of heat exchanger 260a. Chilled water inlet 62 from cooling bath 40 and heated water outlet 68 leading to cooling bath 40 are provided on a cooling bath end of heat exchanger 260b. Pre-heated water outlet 268 of heat exchanger 260a leads to pre-heated water inlet 266 of heat exchanger 260b. Pre-chilled Water outlet 264 of heat exchanger 260b leads to pre-chilled water inlet 262 of heat exchanger 260a. If desired, the tubes leading between heat exchangers 260a and 260b can be routed together in a thermally insulating sleeve to promote even more overall heat exchange between the warmed water returning from therapy pad 20 and the chilled water pumped from cooling bath 40.

In the illustrated embodiment, heat exchangers 260a and 260b are counter-current heat exchangers. In one embodiment, for heat exchanger 260a, shell flow from heated water inlet 66 to pre-heated water outlet 268 along (e.g., serpentine) pathway 290a is generally counter-current to tube flow from pre-chilled water inlet 262 to chilled water outlet 64 along tube paths 292a. Likewise, for heat exchanger 260b, shell flow from pre-heated water inlet 266 to heated water outlet 68 along (e.g., serpentine) pathway 290b is generally counter-current to tube flow from chilled water inlet 62 to pre-chilled water outlet 264 along tube paths 292b. Shell and tube flow can be alternatively reversed, as has been described herein, for either one or both heat exchangers 260a and 260b. Further alternatively, either one Or both heat exchangers 260a and 260b can be configured as a co-current heat exchanger.

Housing/Heat Exchanger

Pump Mounting

Figure 7:
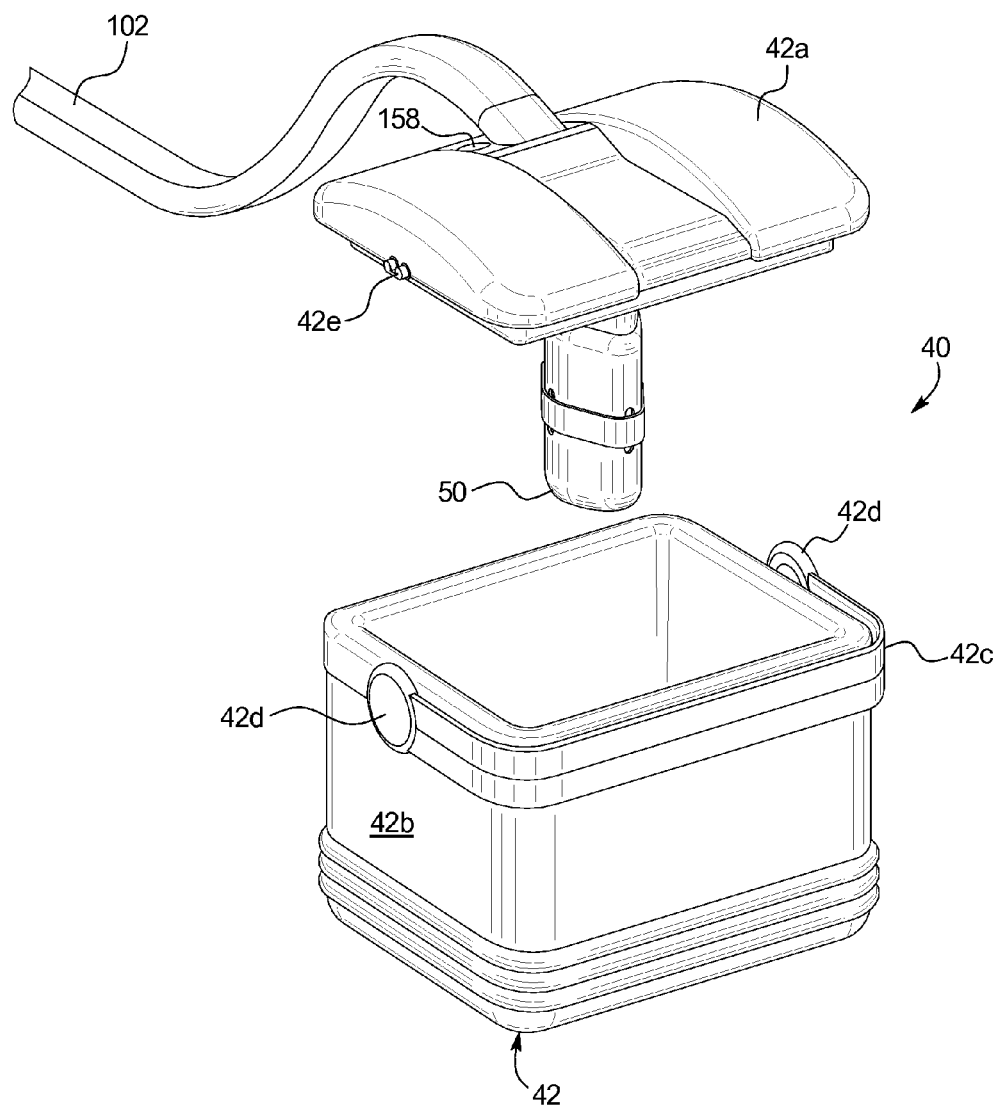
FIG. 7 is a perspective view of one embodiment of a cooling bath housing and liquid pump arrangement for the cold therapy systems and methods of the present disclosure.
Figure 8:
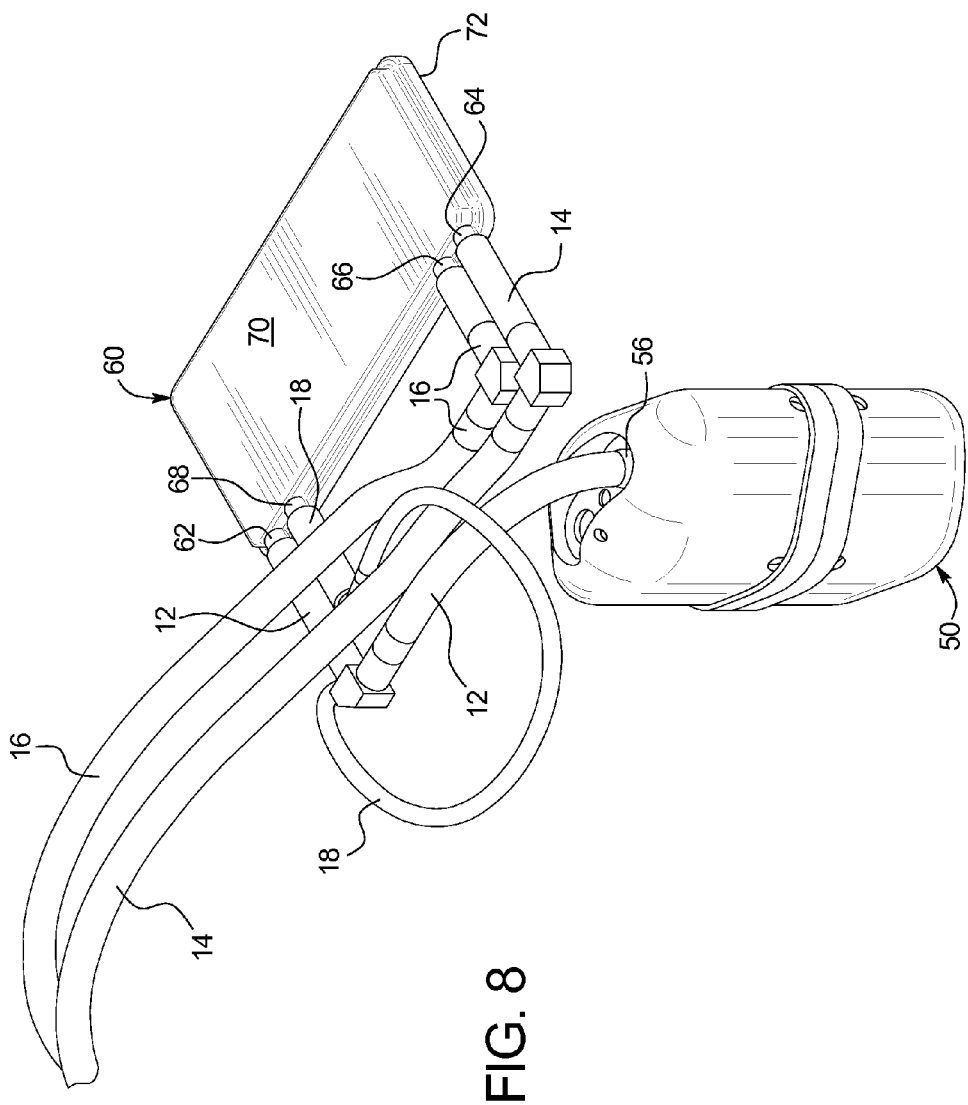
FIG. 8 is a perspective view of one embodiment of the present disclosure for assembling the liquid pump and heat exchanger.
Figure 9:
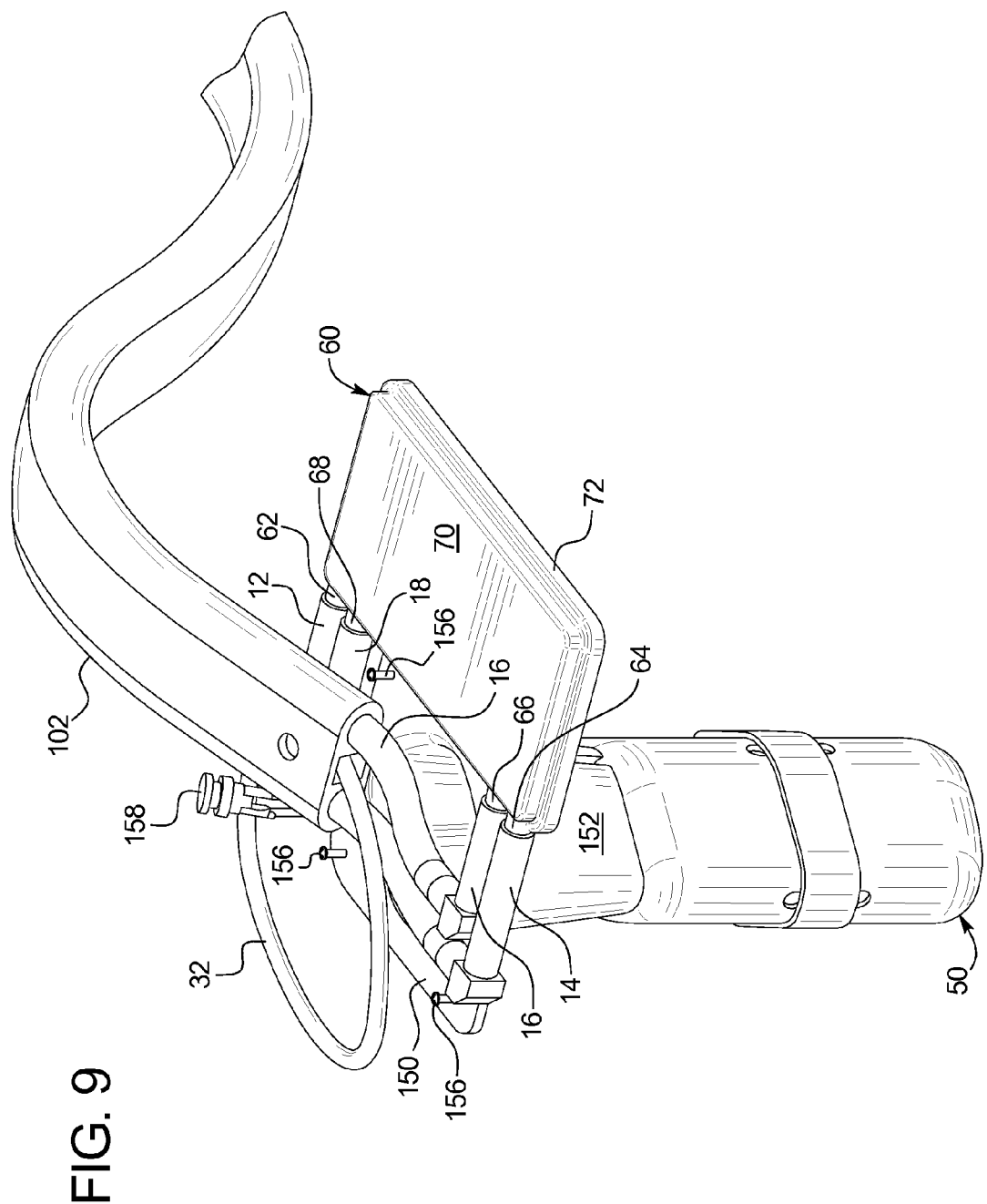
FIG. 9 is a perspective view of one embodiment of the present disclosure for assembling the liquid pump and heat exchanger of the present disclosure along with a bypass return line and a thermally insulating sleeve.

Referring now to FIGS. 7 to 10, one embodiment for bath housing 40 and its integration of liquid pump 50 and heat exchanger 60 is illustrated. FIG. 8 does not show bypass return branch 32, reflecting fixed restrictor system 10. FIG. 9 shows bypass return branch 32 provided with variable temperature system 110. It should be appreciated that FIGS. 7 to 10 and associated written description, except for by-pass return branch 32, are otherwise equally applicable to either system 10 or 110.

FIG. 7 illustrates that housing 42 can have a completely removable lid 42a as opposed to the hinged lid 42a shown in FIG. 3. Base 42b of housing 42 includes a rotating handle 42c. Handle 42c rotates about circular hinges 42d connected to base 42b. In one embodiment, circular hinges 42d include locking features (not seen) that lock with mating features 42e of removable lid 42a, such that lid 42a is locked to base 42b when handle 42c is rotated to a fully upright position.

As illustrated in FIG. 7, lid 42a holds pump 50 such that the pump extends vertically downward into the liquid/ice held in base 42b. The inlet of pump 50 is at the bottom of the pump in one embodiment, such that when pump 50 is positioned operably within base 42b, the pump inlet is located advantageously near the bottom of base 42b. Locating the pump inlet near the bottom of base 42b helps the cold therapy system to operate even when the user does not fill the liquid/ice to the suggested level. The location also helps the pump, heat exchanger(s) and associated tubing to prime and run smoothly when the user does fill the liquid/ice to the suggested level due to a desirable head pressure above the pump inlet.

FIG. 7 also illustrates insulating sleeve 102 exiting lid 42a and extending flexibly to therapy pad 20 (system 10) or to control station 100 (system 110). FIG. 7 illustrates insulating sleeve 102 bending readily up or down. It should be appreciated that insulating sleeve 102 can also twist so as to be maneuverable side to side to allow freedom for the user to locate therapy pad 20 relative to base 42b for treatment. The locking of lid 42a to base 42b and the weight of cooling bath 40 when loaded with water/ice make the cooling bath 40 relatively impervious to torsional forces that the user applies to cooling bath 40 via the twisting of insulating sleeve 102.

FIG. 8 illustrates one embodiment for locating-heat exchanger 60 in close proximity to pump 50. Bath-exchanger pathway 12 extends from the outlet 56 of pump 50 to chilled water inlet 62 of heat exchanger 60. In the illustrated embodiment, an elbow fitting is used to allow bath-exchanger pathway 12 to make a sharp ninety degree turn. The elbow fitting (as with the other illustrated elbow fittings shown in FIGS. 8 to 10) could be excluded in other embodiments. In any case, the overall length of bath-exchanger pathway 12 is kept relatively short so that heat exchanger 60 and pump 50 can be grouped closely together. In the illustrated embodiment, heat exchanger 60 is mounted generally horizontally and at a right angle to the generally vertically disposed pump 50.

FIG. 8 also illustrates that exchanger-bath pathway 18 extends from heated water outlet 68 of heat exchanger 60 downward into housing 42 of cooling bath 40. In an embodiment, exchanger-bath pathway 18 runs to a barbed outlet fitting (not illustrated) fitted to a bottom plate 142 (FIG. 10) Of housing lid 42a. The barbed fitting opens to the water/ice of bath 40. Exchanger-pad pathway 14 extends from chilled water outlet 64 of heat exchanger 60 to patient therapy pad 20 (directly or via control station 100). Pad-exchanger pathway 16 extends from pad 20 (directly or via control station 100) to heated water inlet 66 of heat exchanger 60. Heat exchanger 60 is mounted with shell tray 70 located above shell cover 72, however, shell cover 72 could alternatively be located above shell tray 70.

FIG. 9 illustrates the tubing arrangement described in connection with FIG. 8 but also shows exchanger-pad pathway 14 and pad-exchanger pathway 16 routed within insulting sleeve 102. Further, bypass return branch 32 of system 110 is shown returning from diverter valve 30 (not seen here) and exiting from insulting sleeve 102 into housing 42 of cooling bath 40. Although not shown here, it is contemplated in one embodiment to run the smaller diameter tubing of reduced exchanger-bath pathway 18 through an aperture formed in the back of insulting sleeve 102 and out the end of insulting sleeve 102, coextensive with bypass return branch 32. Bypass return branch 32, like exchanger-bath pathway 18, can likewise run to a separate barbed outlet fitting (not illustrated) fitted to a bottom plate 142 (FIG. 10) of housing lid 42a, allowing bypassed water returning from therapy pad 20 to flow directly to the water/ice of bath 40.

FIG. 9 also illustrates standoff flange 150. Standoff flange 150 is formed with an elliptically or diamond shaped standoff 152 that terminates with a shape that receives pump 50 firmly around at least substantially all of the top circumference of the pump housing. The bottom of standoff 152 removeably attaches to the top of pump 50 in one embodiment, e.g., via bonding, one or more fastener, snap-fitting interconnecting features at the bottom of standoff 152 and the top of pump 50, and any combination thereof. Alternatively, pump 50 is pulled taught into the bottom of standoff 152 via the connection of pump 50 to heat exchanger 60 via bath-exchanger pathway 12. In any case, the vertical length of standoff 152 is set such that when standoff flange 150 is fastened to the lid 42a of bath housing 42, pump 50 is positioned properly vertically for operation within bath housing 42 when lid 42a is connected to base 42b.

Figure 10:
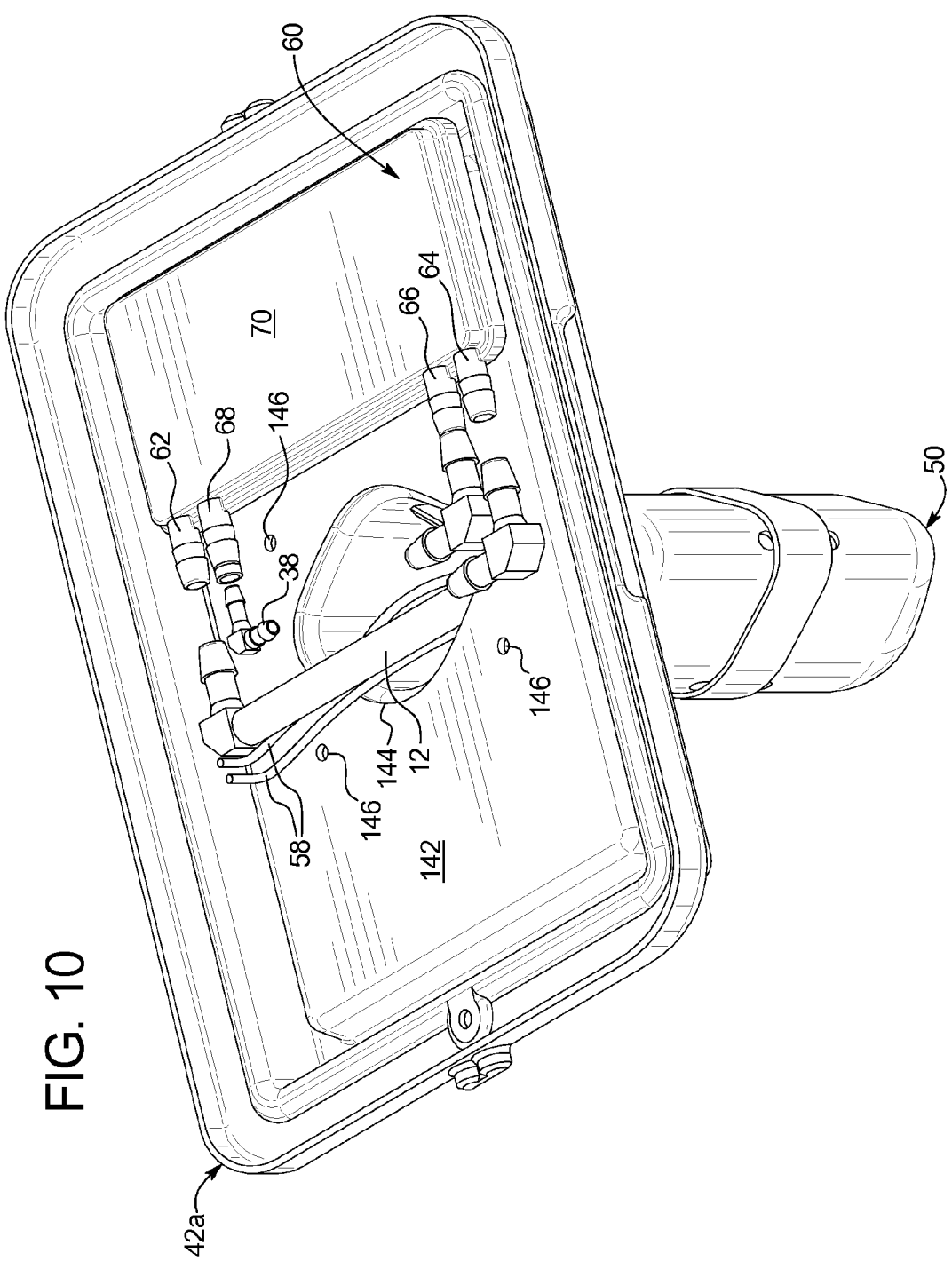
FIG. 10 is a perspective view of one embodiment of the present disclosure for mounting the pump and heat exchanger with the cooling bath housing.

Standoff flange 150 defines mounting holes for receiving mounting fasteners 156. FIG. 10 illustrates that housing lid 42a includes a bottom plate 142 that defines holes 146 for mating with the mounting holes of standoff flange 150. Holes 146 can be threaded or secure threaded inserts for threadingly receiving mounting fasteners 156 from the bottomside of standoff flange 150. Fasteners 156 can alternatively secure to nuts. Still further alternatively, standoff 152 depends directly from bottom plate 142. In the illustrated embodiment, however, bottom plate 142 defines an aperture 144 that at least substantially matches the size and shape of the opening at the top of standoff 152. Aperture 144 allows bath-exchanger pathway 12 to extend into lid 42a to heat exchanger 60 and for pump power wires 58 to (i) extend through sleeve 102 to control station 100 or (ii) extend as illustrated in FIG. 9 to a water-proof electrical connector 158 for mating with a plug (or plug connector) located on at top of lid 42a. Water-proof electrical connector 158 still further alternatively terminates directly at an external plug as seen in FIG. 7.

FIG. 10 also illustrates fixed restrictor 38, which as described above is provided with both fixed and variable temperature systems 10 and 110. Restrictor 38 results in a reduced diameter tube 18 exiting the restrictor and extending through aperture 144, into standoff 152. Standoff 152 is provided with openings (not illustrated) such that exchanger-bath pathway 18 can terminate within standoff 152, wherein water from exchanger-bath pathway 18 can flow through the openings to mix with the water/ice of bath 40. Alternatively, exchanger-bath tubing 18 extends itself through one of the openings of standoff 152 into the water/ice of bath 40. Bypass return branch 32 of system 110 can also return itself or its water to the water/ice of bath 40 through standoff 152 via any of the alternatives discussed with exchanger-bath pathway 18.

FIG. 10 illustrates that in general only one-half of lid 42a is occupied. It is accordingly contemplated to provide a second like-sized heat exchanger (or two smaller heat exchangers), e.g., in series, such as heat exchangers 260a and 260b of FIG. 6, in the other, unused half of lid 42a. Although not illustrated, lid 42a can have features (e.g., snap-fit tongue and groove or locking tab) that hold the one or more heat exchanger removeably in place.

Operation

It has been found through various experimentation that the heat exchanger of the present disclosure can control the temperature of fluid flowing through therapy pad 20, such that the temperature rarely if ever drops below 40° Fahrenheit. The experimentation has been confirmed through modeling. Here, calculations were made using a required energy from seventy-five watt-hours to one-hundred fifty watt-hours. An average sized patient appears to be able to generate about one-hundred fifty watt-hours or heat with pad 20 being applied for example to the patient's knee. Energy generation drops to approximately one hundred watt-hours after the patient has been cold-soaked for about twenty minutes. Older patients with less body mass and reduced circulation can produce as little as seventy-live watt-hours of heat for a pad 20 applied again to the knee. The estimates are based on temperature drop across pad 20 at various flowrates in the range of 40° F. (4.4° C.) to 50° F. (10° C.).

The cold therapy systems described herein attempt to provide a therapy pad 20 temperature of no less than 38° F. (3.3° C.) with 40° F. (4.4° C.) as a desired minimum. One desirable temperature range in the therapy pad 20 is 40° F. (4.4° C.) to 52° F. (11.1° C.) depending mostly on patient size and metabolic rate. Such an operating range results in a safe unit in which an average bath 40 water temperature of 34° F. (1.1° C.) can be safely raised to a pad inlet temperature of 40° F. (4.4° C.) to 42° F. (5.6° C.) and is warmed by the patient to 50° F. (10° C.) to 52° F. (11.1° C.) before the water is returned back to heat exchanger 60, 160 or 260a.

Additional Aspects of the Present Disclosure

Aspects of the subject matter described herein may be useful alone or in combination one or more other aspect described herein. Without limiting the foregoing description, in a first aspect of the present disclosure, a cold therapy system includes a cooling bath; a therapy pad; a heat exchanger; a first pathway fluidly connecting the cooling bath to the heat exchanger; a second pathway fluidly connecting the heat exchanger to an inlet of the therapy pad; a third pathway fluidly connecting an outlet of the therapy pad to the heat exchanger; and a fourth pathway fluidly connecting an outlet of the heat exchanger to the cooling bath.

In accordance with a second aspect of the present disclosure, which may be used in combination with the first aspect, the cold therapy system includes a pump for pumping fluid from the cooling bath, through the therapy pad, through the heat exchanger, back to the cooling bath.

In accordance with a third aspect of the present disclosure, which may be used in combination with the second aspect, the pump is submerged in the cooling bath.

In accordance with a fourth aspect of the present disclosure, which may be used in combination with any one or more of the preceding aspects, the heat exchanger is affixed to the cooling bath.

In accordance with a fifth aspect of the present disclosure, which may be used in combination with any one or more of the preceding aspects, the heat exchanger is submerged in the water/ice of the cooling bath.

In accordance with a sixth aspect of the present disclosure, which may be used in combination with any one or more of the preceding aspects, the heat exchanger is a shell and tube heat exchanger.

In accordance with a seventh aspect of the present disclosure, which may be used in combination with the sixth aspect, the heat exchanger is arranged such that chilled fluid from the cooling pad flows through at least one tube of the shell and tube heat exchanger while warmed fluid from the therapy pad flows outside the at least one tube.

In accordance with an eighth aspect of the present disclosure, which may be used in combination with the sixth aspect, the heat exchanger is arranged such that warmed fluid from the therapy pad flows through at least one tube of the shell and tube heat exchanger while chilled fluid from the cooling bath flows outside the at least one tube.

In accordance with a ninth aspect of the present disclosure, which may be used in combination with any one or more of the preceding aspects, the cold therapy system includes a temperature sensor operable with the second pathway and which outputs to a temperature display.

In accordance with a tenth aspect of the present disclosure, which may be used in combination with any one or more of the preceding aspects, the cold therapy system includes a fixed restrictor positioned to create backpressure for inflating the therapy pad.

In accordance with an eleventh aspect of the present disclosure, which may be used in combination with any one or more of the preceding aspects, the cold therapy system includes a bypass pathway fluidly connecting the third pathway to the cooling pad and a valve positioned and arranged to proportion fluid flowing through the third fluid pathway and the bypass pathway.

In accordance with a twelfth aspect of the present disclosure, which may be used in combination with the eleventh aspect, the valve varies a backpressure of the fluid to proportion the fluid.

In accordance with a thirteenth aspect of the present disclosure, which may be used in combination with the eleventh aspect, the valve is placed in the bypass pathway.

In accordance with a fourteenth aspect of the present disclosure, which may be used in combination with any one or more of the preceding aspects, a cold therapy system includes a cooling bath; a therapy pad; a heal exchanger; a sleeve extending between the heat exchanger and the therapy pad; a first pathway fluidly connecting an outlet of the heat exchanger to an inlet of the therapy pad; and a second pathway fluidly connecting an outlet of the therapy pad to an inlet of the heat exchanger, wherein the first and second fluid pathways are located within the sleeve.

In accordance with a fifteenth aspect of the present disclosure, which may be used with any one or more of the preceding aspects in combination with the fourteenth aspect, the sleeve is connected to a control station, the control station including a valve that is maneuvered to adjust a temperature of fluid flowing through the therapy pad.

In accordance with a sixteenth aspect of the present disclosure, which may be used with any one or more of the preceding aspects in combination with the fifteenth aspect, the valve is a diverting valve placed in one of the second fluid pathway and a bypass branch teed off of the second fluid pathway, the bypass branch bypassing the heat exchanger and running to the cooling bath.

In accordance with a seventeenth aspect of the present disclosure, which may be used with the sixteenth aspect, the bypass line is run within the sleeve.

In accordance with an eighteenth aspect of the present disclosure, which may be used with the fifteenth aspect, the cold therapy includes a temperature sensor housed by the control station and in fluid communication with the first fluid pathway.

In accordance with a nineteenth aspect of the present disclosure, which may be used in combination with any one or more of the preceding aspects, a cold therapy unit method includes (i) chilling water, (ii) flowing the chilled water to absorb heat from warmed water returning from a therapy pad, (iii) flowing the heat-absorbed chilled water through the therapy pad becoming warmed water, (iv) flowing the warmed water to deliver heat to incoming chilled water, and (v) flowing the heat delivering warmed water to be re-chilled.

In accordance with a twentieth aspect of the present disclosure, which may be used with any one or more of the preceding aspects in combination with the nineteenth aspect, the cold therapy unit method includes maintaining the heat-absorbed chilled water at or above forty degrees Fahrenheit.

In accordance with a twenty-first aspect of the present disclosure, which may be used with any one or more of the preceding aspects in combination with the nineteenth aspect, the cold therapy unit method includes splitting the warmed water so that a first portion performs (iii) and a second portion is directly re-chilled.

In accordance with a twenty-second aspect of the present disclosure, which may be used in combination with any one or more of the preceding aspects, a cold therapy system includes a cooling bath including a housing for storing a cooling fluid; a therapy pad for placement on a user to cool the user; and a heat exchanger for exchanging heat acquired from a user with cooling fluid flowing from the cooling bath to the therapy pad, the heat exchanger carried by a wall of the housing of the cooling bath.

In accordance with a twenty-third aspect of the present disclosure, which may be used with any one or more of the preceding aspects in combination with the twenty-second aspect, the heat exchanger is located within the wall of the housing.

In accordance with a twenty-fourth aspect of the present disclosure, which may be used with any one or more of the preceding aspects in combination with the twenty-second aspect, the wall is a moveable lid of the housing.

In accordance with a twenty-fifth aspect of the present disclosure, any of the structure and functionality illustrated and described in connection with FIG. 1 may be used in combination with any one or more of the preceding aspects.

In accordance with a twenty-sixth aspect of the present disclosure, any of the structure and functionality illustrated and described in connection with FIG. 2 may be used in combination with any one or more of the preceding aspects.

In accordance with a twenty-seventh aspect of the present disclosure, any of the structure and functionality illustrated and described in connection with FIG. 3 may be used in combination with any one or more of the preceding aspects.

In accordance with a twenty-eighth aspect of the present disclosure, any of the structure and functionality illustrated and described in connection with FIGS. 4A and 4B may be used in combination with any one or more of the preceding aspects.

In accordance with a twenty-ninth aspect of the present disclosure, any of the structure and functionality illustrated and described in connection with FIG. 5 may be used in combination with any one or more of the preceding aspects.

In accordance with a thirtieth aspect of the present disclosure, any of the structure and functionality illustrated and described in connection with FIG. 6 may be used in combination with any one or more of the preceding aspects.

In accordance with a thirty-first aspect of the present disclosure, any of the structure and functionality illustrated and described in connection with FIG. 7 may be used in combination with any one or more of the preceding aspects.

In accordance with a thirty-second aspect of the present disclosure, any of the structure and functionality illustrated and described in connection with FIG. 8 may be used in combination with any one or more of the preceding aspects.

In accordance with a thirty-third aspect of the present disclosure, any of the structure and functionality illustrated and described in connection with FIG. 9 may be used in combination with any one or more of the preceding aspects.

In accordance with a thirty-fourth aspect of the present disclosure, any of the structure and functionality illustrated and described in connection with FIG. 10 may be used in combination with any one or more of the preceding aspects.

It should be understood that various changes and modifications to the presently preferred embodiments described The invention is claimed as follows:

1. A cold therapy system comprising:
   a cooling bath;
   a therapy pad;
   a heat exchanger;
   a first pathway fluidly connecting the cooling bath to the heat exchanger;
   a second pathway fluidly connecting the heat exchanger to an inlet of the therapy pad;
   a third pathway fluidly connecting an outlet of the therapy pad to the heat exchanger; and
   a fourth pathway fluidly connecting an outlet of the heat exchanger to the cooling bath, wherein the first, second, third and fourth pathways are fluidly connected to the heat exchanger such that chilled fluid from the cooling bath receives heat from warmed fluid returning from the therapy pad.

2. The cold therapy system of claim 1, which includes a pump for pumping fluid from the cooling bath, through the therapy pad, through the heat exchanger, back to the cooling bath.

3. The cold therapy system of claim 2, wherein the pump is submerged in the cooling bath.

4. The cold therapy system of claim 1, wherein the heat exchanger is affixed to the cooling bath.

5. The cold therapy system of claim 1, wherein the heat exchanger is submerged in the cooling bath.

6. The cold therapy system of claim 1, wherein the heat exchanger is a shell and tube heat exchanger.

7. The cold therapy system of claim 6, wherein the heat exchanger is arranged such that chilled fluid from the cooling bath flows through at least one tube of the shell and tube heat exchanger while warmed fluid from the therapy pad flows outside the at least one tube.

8. The cold therapy system of claim 6, wherein the heat exchanger is arranged such that warmed fluid from the therapy pad flows through at least one tube of the shell and tube heat exchanger while chilled fluid from the cooling bath flows outside the at least one tube.

9. The cold therapy system of claim 1, which includes a temperature sensor operable with the second pathway, the temperature sensor outputting to a temperature display.

10. The cold therapy system of claim 1, which includes a fixed restrictor positioned to create backpressure for inflating the therapy pad.

11. The cold therapy system of claim 1, which includes a bypass pathway fluidly connecting the third pathway to the cooling bath and a valve positioned and arranged to proportion fluid flowing through the third fluid pathway and the bypass pathway.

12. The cold therapy system of claim 11, wherein the valve varies a backpressure of the fluid to proportion the fluid.

13. The cold therapy system of claim 11, wherein the valve is placed in the bypass pathway.

14. A cold therapy system comprising:
    a cooling bath;
    a therapy pad;
    a heat exchanger positioned and arranged to exchange heat acquired from fluid exiting the therapy pad with fluid exiting the cooling bath;
    a sleeve extending between the heat exchanger and the therapy pad;
    a first pathway fluidly connecting an outlet of the heat exchanger to an inlet of the therapy pad; and
    a second pathway fluidly connecting an outlet of the therapy pad to an inlet of the heat exchanger, wherein the first and second fluid pathways are located within the sleeve.

15. The cold therapy system of claim 14, wherein the sleeve is connected to a control station, the control station including a valve that is maneuvered to adjust a temperature of fluid flowing through the therapy pad.

16. The cold therapy system of claim 15, wherein the valve is a diverting valve placed in one of the second fluid pathway and a bypass branch teed off of the second fluid pathway, the bypass branch bypassing the heat exchanger and running to the cooling bath.

17. The cold therapy system of claim 16, wherein the bypass line is run within the sleeve.

18. The cold therapy system of claim 15, which includes a temperature sensor housed by the control station and in fluid communication with the first fluid pathway.

19. A cold therapy system comprising:
    a cooling bath including a housing for storing a cooling fluid;
    a therapy pad for placement on a user to cool the user; and
    a heat exchanger for exchanging heat acquired from a user with cooling fluid flowing from the cooling bath to the therapy pad, the heat exchanger carried by a wall of the housing of the cooling bath.

20. The cold therapy system of claim 19, wherein the heat exchanger is located within the wall of the housing.

21. The cold therapy system of claim 19, wherein the wall is a moveable lid of the housing.

22. A cold therapy unit method comprising:
    (i) chilling water;
    (ii) flowing the chilled water to absorb heat from warmed water returning from a therapy pad,
    (iii) flowing the heat-absorbed chilled water through the therapy pad becoming warmed water,
    (iv) flowing the warmed water to deliver heat to incoming chilled water, and
    (v) flowing the heat delivering warmed water to be re-chilled.

23. The cold therapy unit method of claim 22, which includes maintaining the heat-absorbed chilled water at or above forty degrees Fahrenheit.

24. The cold therapy unit method of claim 22, which includes splitting the warmed water so that a first portion performs (iii) and a second portion is directly re-chilled.

* * * * *